United States Patent
Koike et al.

(10) Patent No.: US 10,520,415 B2
(45) Date of Patent: Dec. 31, 2019

(54) PARTICULATE MATTER DETECTION ELEMENT, PARTICULATE MATTER DETECTION SENSOR, AND METHOD OF MANUFACTURING PARTICULATE MATTER DETECTION ELEMENT

(71) Applicant: DENSO CORPORATION, Kariya, Aichi-pref. (JP)

(72) Inventors: Kazuhiko Koike, Kariya (JP); Hirokatsu Imagawa, Kariya (JP)

(73) Assignee: DENSO CORPORATION, Kariya (JP)

( * ) Notice: Subject to any disclaimer, the term of this patent is extended or adjusted under 35 U.S.C. 154(b) by 483 days.

(21) Appl. No.: 15/110,447

(22) PCT Filed: Jan. 9, 2015

(86) PCT No.: PCT/JP2015/050508
§ 371 (c)(1),
(2) Date: Jul. 8, 2016

(87) PCT Pub. No.: WO2015/105182
PCT Pub. Date: Jul. 16, 2015

(65) Prior Publication Data
US 2016/0334321 A1    Nov. 17, 2016

(30) Foreign Application Priority Data

Jan. 10, 2014   (JP) ................................ 2014-002882

(51) Int. Cl.
*G01N 37/00*    (2006.01)
*G01N 15/06*    (2006.01)
(Continued)

(52) U.S. Cl.
CPC ...... *G01N 15/0656* (2013.01); *G01M 15/102* (2013.01); *G01N 15/0606* (2013.01); *G01N 2015/0046* (2013.01)

(58) Field of Classification Search
USPC ....................... 324/464, 71.4, 693
See application file for complete search history.

(56) References Cited

U.S. PATENT DOCUMENTS 5,008,628 A * 4/1991 Krigmont ............ G01N 27/043
                                           324/464
8,860,439 B2 * 10/2014 Kimata .................. F01N 11/00
                                           324/464
(Continued)

FOREIGN PATENT DOCUMENTS

JP        60-196659        10/1985
JP        2012-078130      4/2012

OTHER PUBLICATIONS

Asada Mesh Co., Ltd., Asada Mesh Technical Documentation No. 2009, 002-006 (5 pages) and English translation (6 pages).

*Primary Examiner* — Vincent Q Nguyen
(74) *Attorney, Agent, or Firm* — Nixon & Vanderhye P.C.

(57) ABSTRACT

A particulate matter detection element for detecting particulate matter in a gas to be measured includes flat-shaped conductor layers, flat-shaped insulating layers, a laminated structure in which the conductor layers and the insulating layers are alternately laminated, and a detecting unit having the conductor layers of different polarities as a pair of detection electrodes on a cross section of the laminated structure. The conductor layers each have a constant thickness, and include conductor layer planar portions having a stripped-pattern cross section, and tapered conductor layer end edge portions each having a triangular cross section, provided on both sides of the respective conductor layer planar portions.

7 Claims, 19 Drawing Sheets

(51) Int. Cl.
  *G01M 15/10*  (2006.01)
  *G01N 15/00*  (2006.01)

(56) References Cited

U.S. PATENT DOCUMENTS

| | | |
|---|---|---|
| 2009/0051376 A1 | 2/2009 | Schnell et al. |
| 2009/0188300 A1* | 7/2009 | Gualtieri ............. F02D 41/1466 |
| | | 73/28.01 |
| 2010/0072055 A1* | 3/2010 | Tanaka ................... B01D 53/32 |
| | | 204/164 |
| 2012/0103058 A1 | 5/2012 | Maeda et al. |
| 2012/0266646 A1* | 10/2012 | Maeda ................ F02D 41/1466 |
| | | 73/1.06 |
| 2013/0283886 A1 | 10/2013 | Teranishi et al. |

* cited by examiner (COMPARISON EXAMPLE 2)

(EXAMPLE 4)

(COMPARISON EXAMPLE 1)

(EXAMPLE 1)

(EXAMPLE 2)

(EXAMPLE 3)

(COMPARISON EXAMPLE 2)

(EXAMPLE 4)

FIG.5C (EXAMPLE 5)
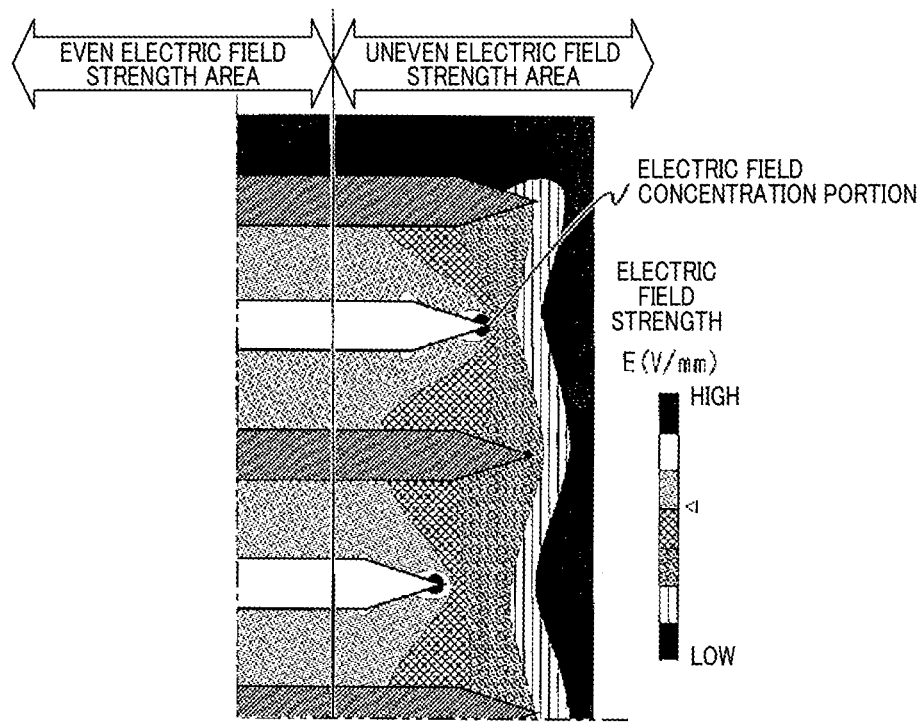
FIG.5D (EXAMPLE 6)
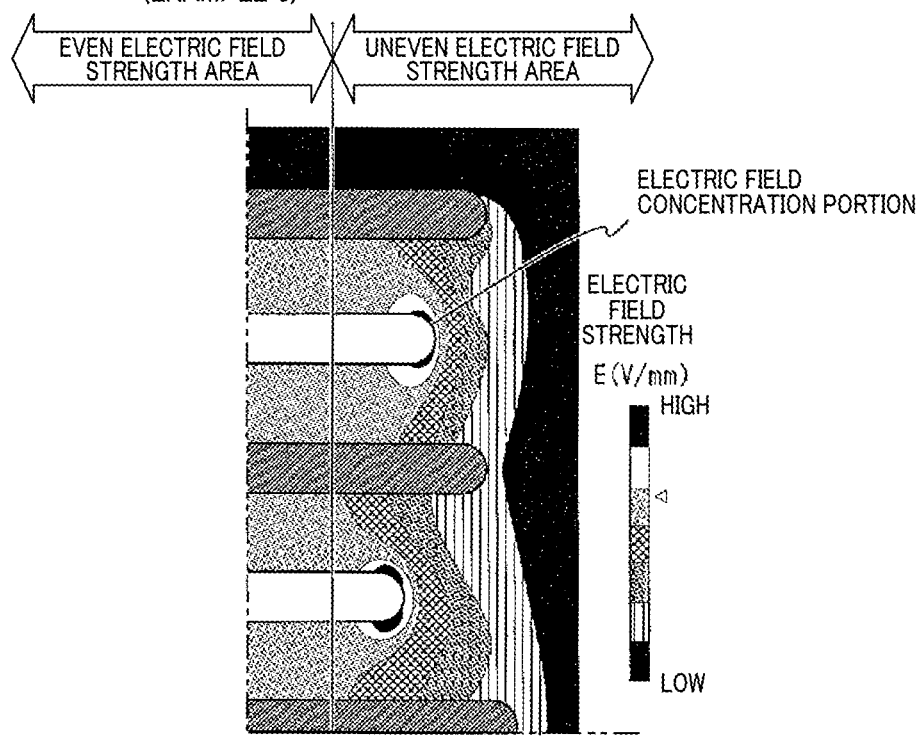

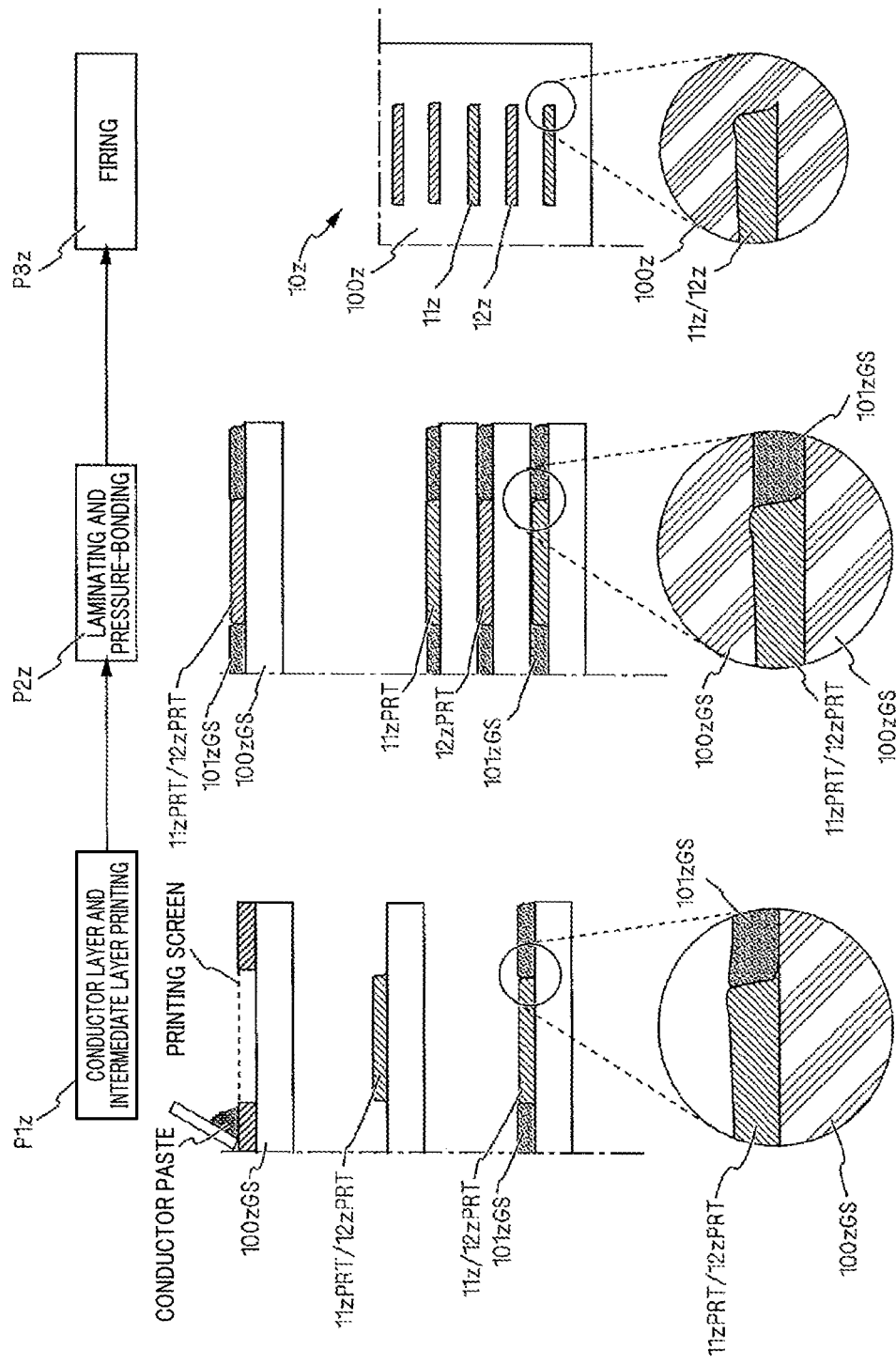

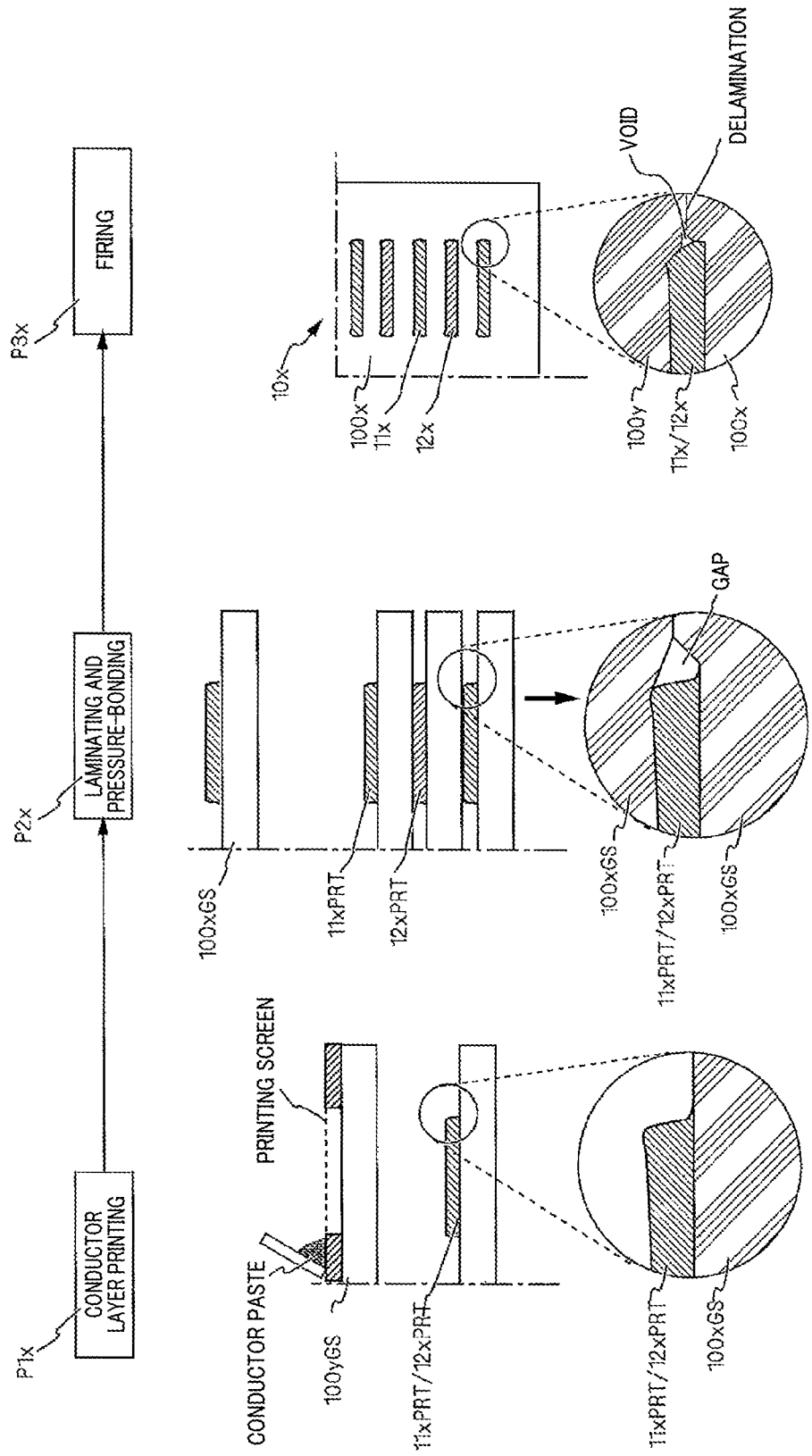

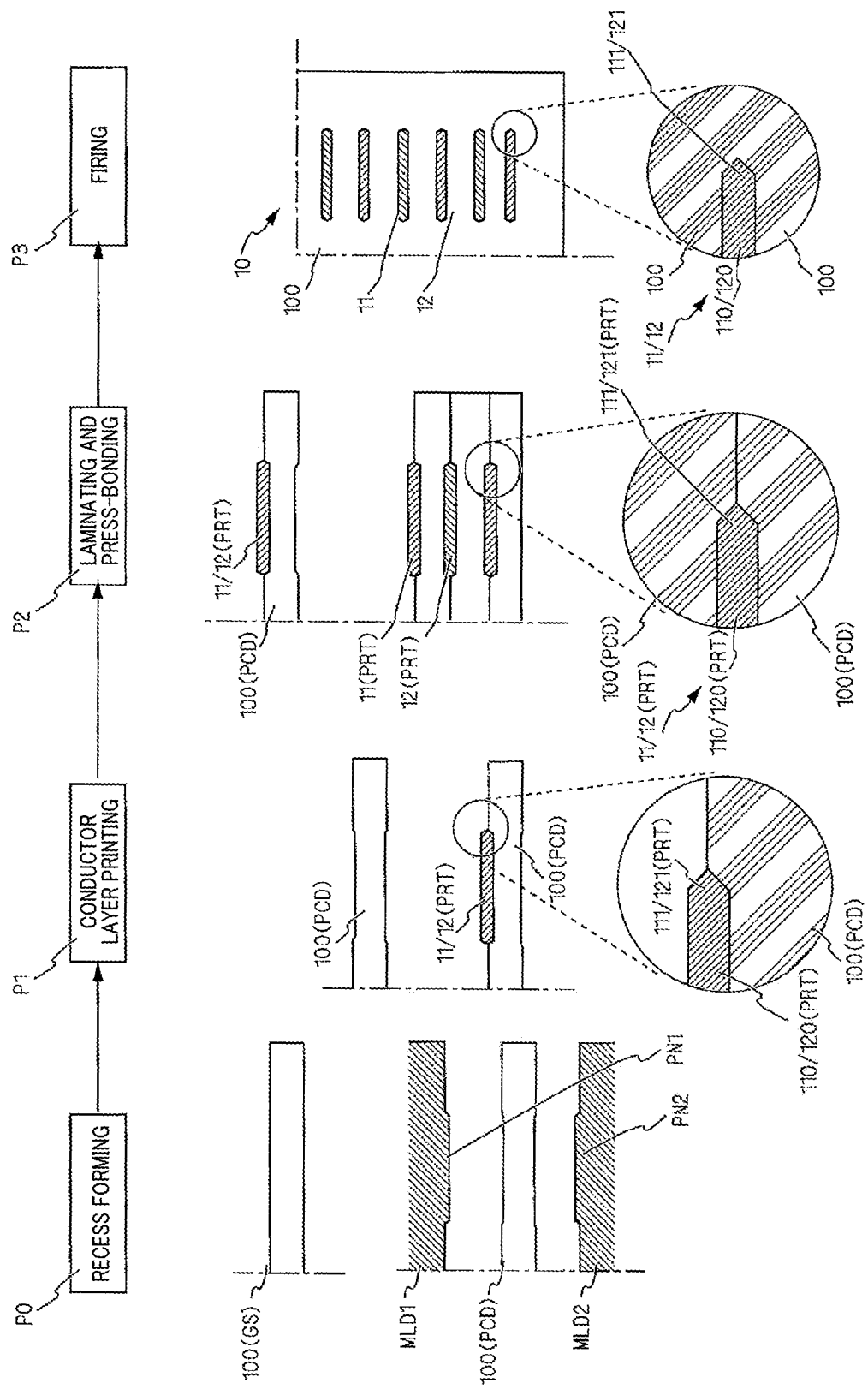

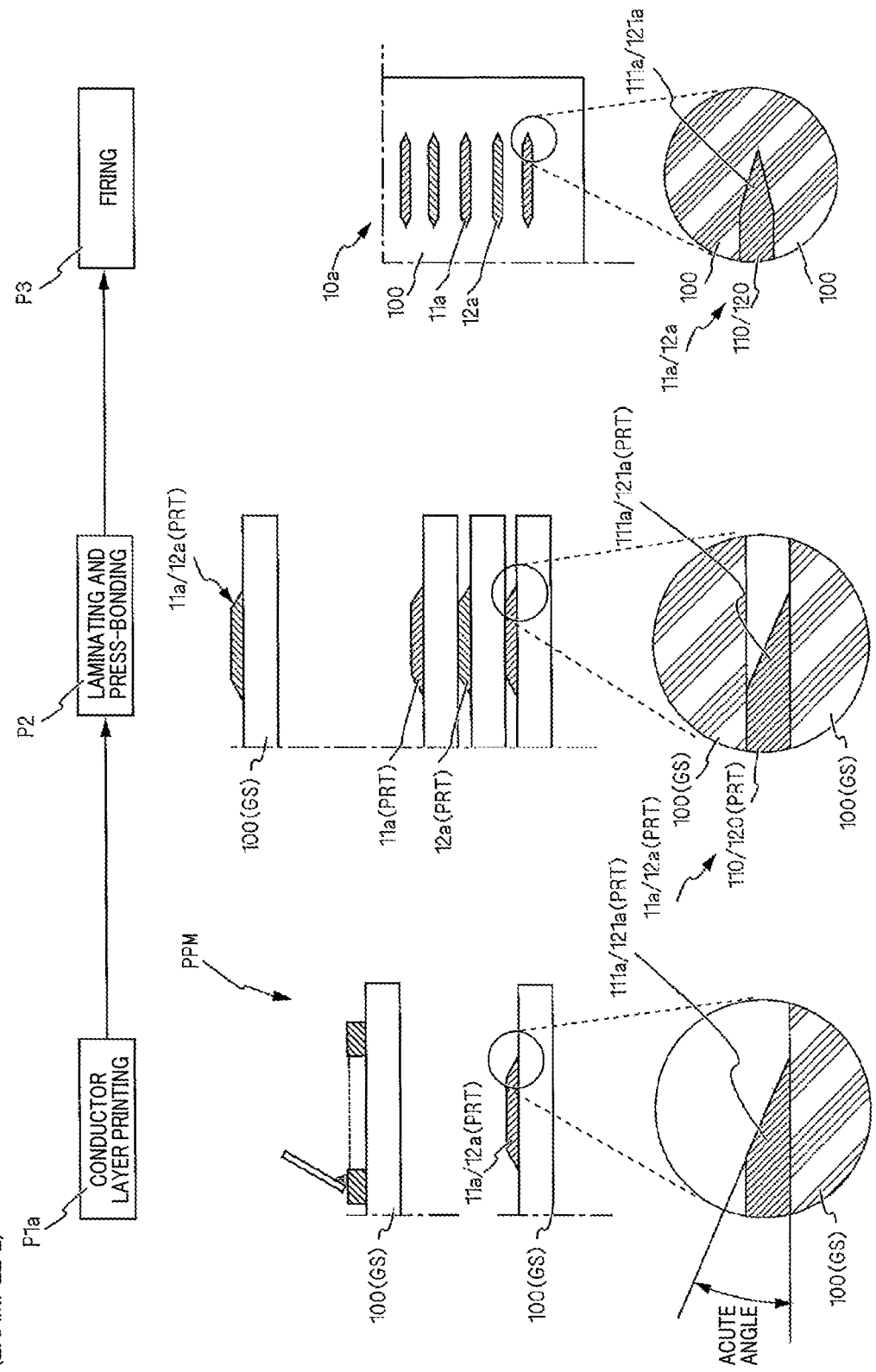

PARTICULATE MATTER DETECTION ELEMENT, PARTICULATE MATTER DETECTION SENSOR, AND METHOD OF MANUFACTURING PARTICULATE MATTER DETECTION ELEMENT

CROSS-REFERENCE TO RELATED APPLICATION

This application is the U.S. national phase of International Application No. PCT/JP2015/050508, filed 9 Jan. 2015, which designated the U.S. and is based on and claims the benefit of priority from earlier Japanese Patent Application No. 2014-2882 filed Jan. 10, 2014, the description of each of which are incorporated herein by reference.

BACKGROUND OF THE INVENTION

Technical Field

The present disclosure relates to a particulate matter detection element favorably used for an exhaust gas purification system of a vehicle internal combustion engine to detect particulate matter present in an exhaust gas that is a gas to be measured, and relates to a particulate matter detection sensor, and a method of manufacturing the particulate matter detection element.

Background Art

Particulate matter detection sensors that detect particulate matter in various gases to be measured have been proposed. In such a particulate matter detection sensor, a pair of electrodes are formed on a surface of a substrate having insulating properties. Taking advantage of particulate matter having electrical conductivity, the particulate matter detection sensor senses changes in electrical characteristics, such as resistance and capacitance, caused by particulate matter being deposited between the pair of electrodes to thereby detect the particulate matter contained in a gas to be measured, such as a combustion exhaust gas of an internal combustion engine.

For example, a patent literature JP-A-2008-502892 discloses a sensor element in which a pair of comb-shaped electrodes are formed on an insulated substrate such as of alumina ceramic.

In the sensor element of the patent literature mentioned above, a voltage is applied across the pair of electrodes from a power supply unit to form a non-uniform electric field in a space between the comb-shaped electrodes meshing with each other. Thus, soot particles contained in an exhaust gas passing through the sensor element are attracted to the electrodes and deposited thereon. Detecting the resistance across the electrodes of this moment, the amount of deposited soot can be measured.

On the other hand, a patent literature JP-A-S60-196659 discloses resistance measurement electrodes for use in a sensor. The resistance measurement electrodes have a laminated structure in which conductor layers and insulating layers are alternately laminated using thick-film printing and green sheets to accurately form electrodes with a distance of 50 μm or less therebetween, which has been difficult to achieve with conventional thick-film printing. A cross section of the laminated structure is used as the resistance measurement electrodes, with the conductor layers serving as the electrodes. The patent literature JP-A-S60-196659 discloses that the distance between the electrodes can be reduced to about 10 μm which is determined by the thickness of the insulating layer.

CITATION LIST

Patent Literature

[PTL 1] JP-A-2008-502892
[PTL 2] JP-A-S60-196659

A laminated structure can be formed by alternately laminating conductor layers and insulating layers, with the conductor layers being exposed to a cross section of the laminated structure for use as a pair of electrodes as disclosed in JP-A-S60-196659. With this structure, a voltage can be applied across the electrodes to form an electric field to deposit particulate matter between the electrodes as disclosed in JP-A-2008-502892. However, in this case, electric charge is concentrated at corners of the electrode end portions.

It has been found that such electric charge concentration tends to cause particulate matter to be locally deposited near the electrode end portions where electric field intensity is high. Thus, there is a concern that the differences between the masses to which the detection is sensitive and insensitive is increased and detection accuracy is deteriorated.

Hence it is desired to provide a particulate matter detection element having a laminated structure in which flat-shaped conductor layers and flat-shaped insulating layers are alternately laminated, the structure having a cross section where the conductor layers are exposed as a pair of electrodes to configure a detecting unit, with each electrode layer end portion being in a characteristic shape to minimize electric field concentration thereon, to provide a particulate matter detection sensor that uses the particulate matter detection element to form an electric field by applying a high voltage across the pair of electrodes to collect particulate matter, while detecting electrical characteristics changing with the amount of particulate matter in a gas to be measured deposited between the electrodes to highly accurately detect the particulate matter, and to provide a method of manufacturing the particulate matter detection element that minimizes concentration of electric charge on the electrode end portion to realize high detection accuracy.

A particulate matter detection element of the present disclosure has a laminated structure in which flat-shaped conductor layers and flat-shaped insulating layers are alternately laminated. Using a cross section of the laminated structure, a detecting unit having the conductor layers of different polarities as a pair of detection electrodes is configured. Electrical characteristics changing with the amount of particulate matter deposited in the detecting unit are measured and for use in detecting particulate matter in a gas to be measured. The particulate matter detection element is characterized in that the conductor layers each have a constant thickness, and include conductor layer planar portions having a stripped-pattern cross section, and tapered conductor layer end edge portions each having a triangular cross section, provided on both sides of the respective conductor layer planar portions.

In the present disclosure, the conductor layers may also each have a constant thickness, and include conductor layer planar portions having a stripped-pattern cross section, and gently curved conductor layer end edge portions each having a circular-arc cross section, provided on both sides of the respective conductor layer planar portions.

Effects of the Invention

According to the present disclosure, electric field concentration is minimized in the conductor layer end edge portions, and variation in insensible mass due to local deposition of particulate matter is minimized in electric field concentration portions. Therefore, a particulate matter detection element having stable detection accuracy can be realized.

BRIEF DESCRIPTION OF DRAWINGS

In the accompanying drawings:

FIG. 5C is a schematic diagram illustrating electric field intensity distribution on a detecting unit plane, according to example 5;

FIG. 5D is a schematic diagram illustrating electric field intensity distribution on a detecting unit plane, according to example 6;

FIG. 8A is a schematic diagram illustrating a manufacturing process, according to comparative example 1;

FIG. 8B is a schematic diagram illustrating a manufacturing process, according to comparative example 3;

FIG. 8C is a schematic diagram illustrating a manufacturing process, according to example 1 of the present disclosure;

FIG. 8D is a schematic diagram illustrating a manufacturing process, according to example 2 of the present disclosure;

DETAILED DESCRIPTION OF PREFERRED EMBODIMENTS

Figure 1A:
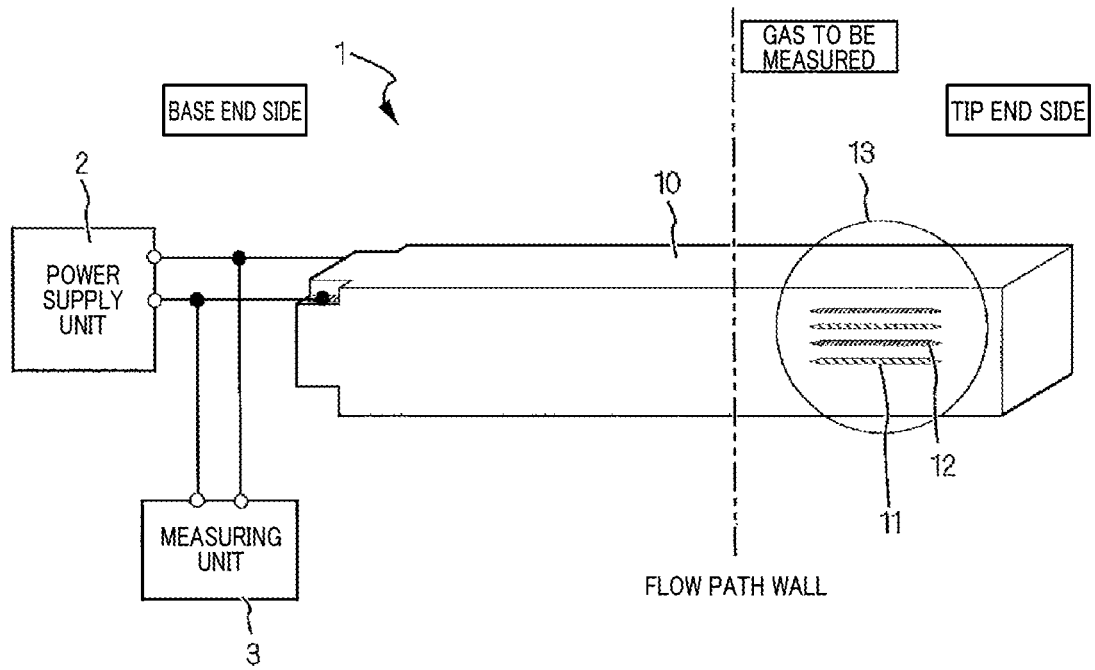
FIG. 1A is a schematic diagram illustrating a general configuration of a particulate matter detection sensor 1, according to a first embodiment of the present disclosure.
Figure 1B:
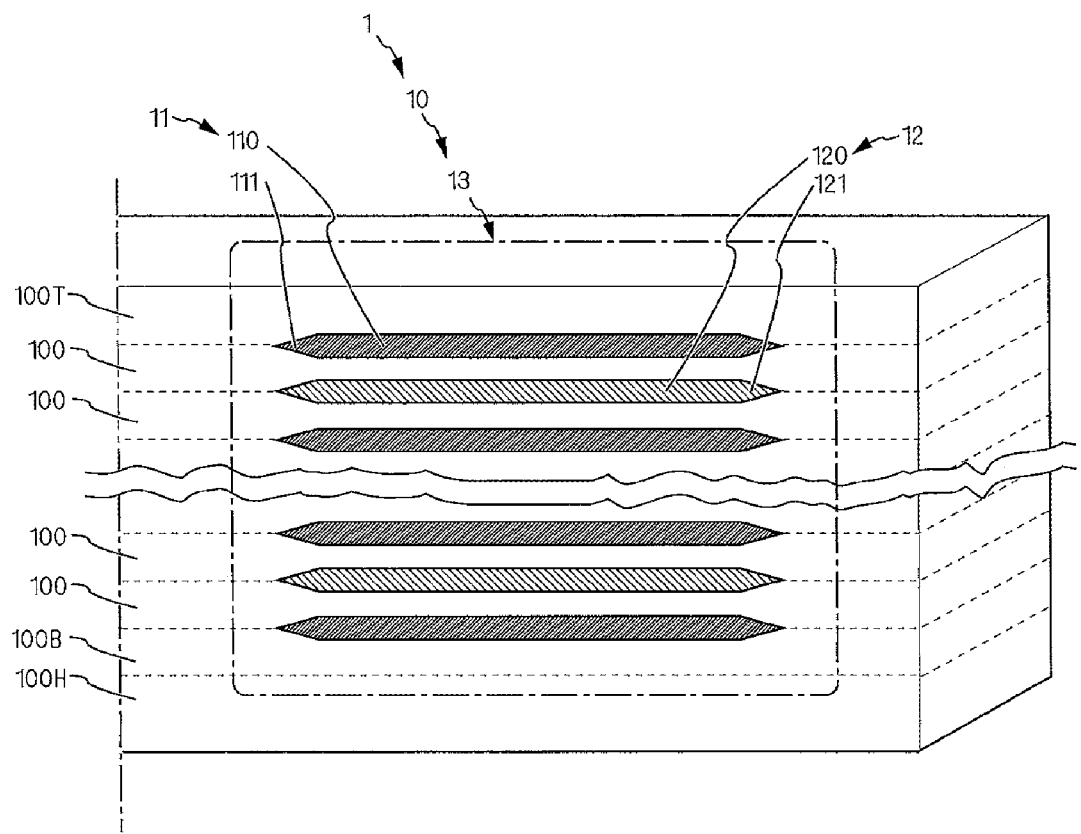
FIG. 1B is an enlarged perspective view illustrating a detecting unit 13 that is a major part of a particulate matter detection element 10 used in the particulate matter detection sensor 1 illustrated in FIG. 1A.
Figure 1C:
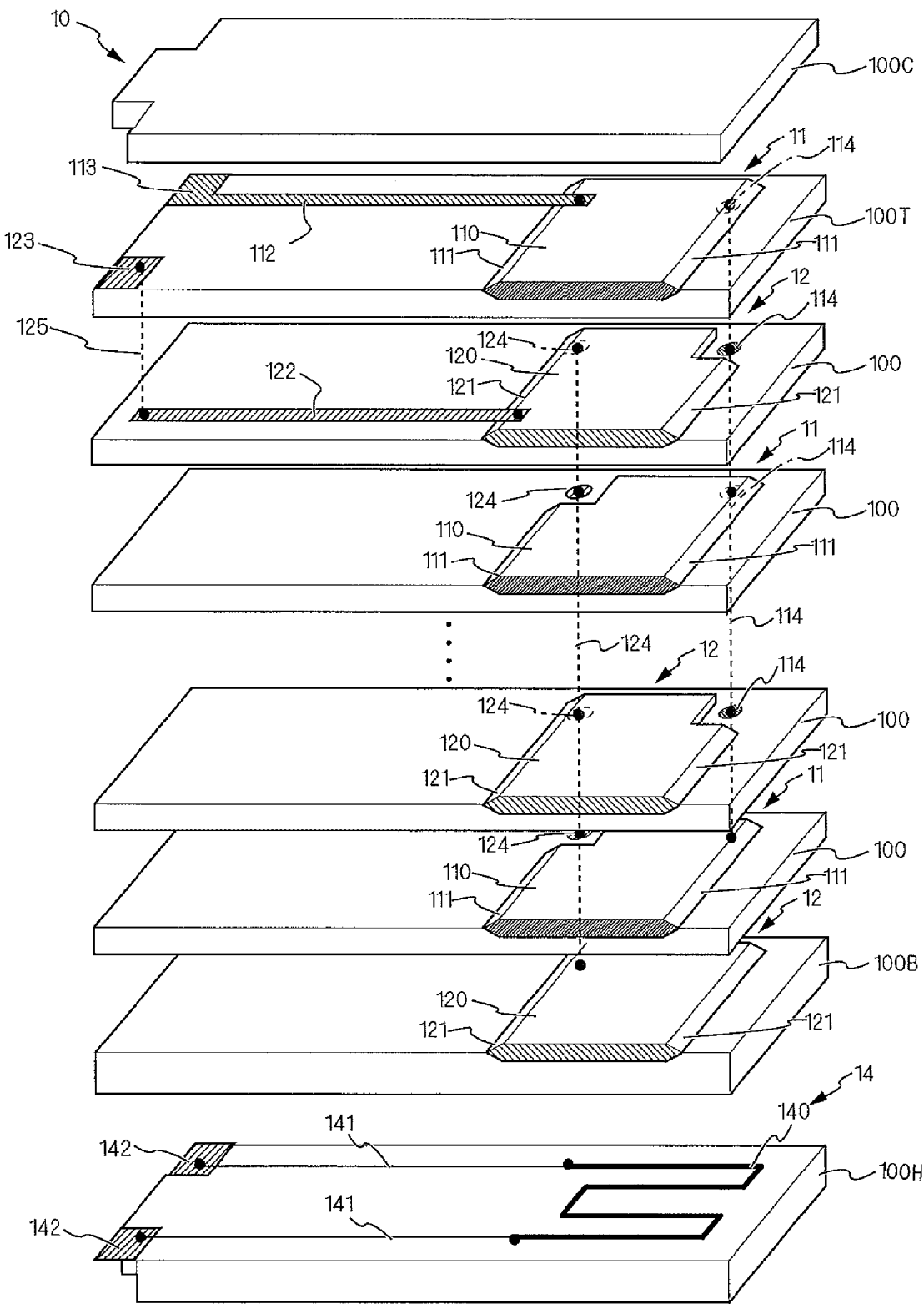
FIG. 1C is an exploded perspective view illustrating an example of an inner structure of the particulate matter detection element 10 used in the particulate matter detection sensor 1 illustrated FIG. 1A.

With reference to FIGS. 1A, 1B, and 1C, hereinafter is described an outline of a particulate matter detection sensor 1 according to a first embodiment of the present disclosure and a particulate matter detection element 10 that is a major part of the present disclosure.

The particulate matter detection sensor 1 (hereafter referred to as sensor 1) of the present disclosure is configured by the particulate matter detection element 10 (hereafter referred to as element 10), a power supply 2, and a measuring unit 3. The element 10 includes a detecting unit 13 which is disposed in a gas to be measured that is an exhaust gas of an internal combustion engine. The power supply 2 applies a predetermined voltage to the element 10. The measuring unit 3 measures electrical characteristics, such as changes in current flowing through the element 10, and changes in voltage and impedance of the element 10, to detect particulate matter in the gas to be measured.

Electrical characteristics changing with the amount of particulate matter deposited in the detecting unit 13 of the element 10 are measured by the measuring unit 3 to detect particulate matter in the gas to be measured.

In the description hereinafter, the element 10 side provided with the detecting unit 13 and exposed to the gas to be measured is referred to as a tip end side. The element 10 side connected to the power supply 2 and the measuring unit 3 is referred to as a base end side.

The sensor 1 can be arranged downstream of a diesel particulate filter (DPF) to detect abnormality of the DPF. Alternatively, the sensor 1 can be arranged upstream of the DPF and used in a system that directly detects particulate matter PM flowing into the DPF.

When the sensor 1 is actually arranged in a flow path of a gas to be measured, a known configuration commonly used as a particulate matter detection sensor including a housing or a cover protecting the detecting unit 13, not shown, can be appropriately used to fix the element 10.

Referring to FIG. 1B, characteristics of the element 10 that is a major part of the present disclosure will be specifically described.

The element 10 has a laminated structure in which flat-shaped conductor layers 11 and 12 and flat-shaped insulating layers 100 are alternately laminated.

The element 10 uses its cross section to configure the detecting unit 13 where the conductor layers 11 and 12 having differing polarities form a pair of detection electrodes.

As shown in FIG. 1B, the detecting unit 13 is configured such that the cross sections of the conductor layers 11 and 12 are alternated, with the insulating layer 100 being interposed between each pair of the conductor layers 11 and 12.

According to the present embodiment, the conductor layers 11 and 12 are characterized in that they each have a constant thickness and include respective conductor layer planar portions 110 and 120 (hereafter referred to as planar portions 110 and 120) and respective conductor layer end edge portions 111 and 121 (hereafter referred to as end edge portions 111 and 121). The planar portions 110 and 120 have cross sections in a stripped pattern. The end edge portions 111 and 121, which are each tapered and have a triangular cross section, are provided to both sides of the respective conductor layer planar portions 110 and 120.

Since the conductor layer end edge portions 111 and 121 having a triangular cross section are provided to both end edges of the respective conductor layers 11 and 12, the present disclosure can reduce electric field concentration at the end edges of the conductor layers 11 and 12. Thus, particulate matter is prevented from being locally deposited on electric field concentration portions (i.e., portions where electric field is concentrated) and detection accuracy is improved and stabilized.

Known conductive materials can be used as appropriate for the conductor layers 11 and 12. For example, conductive materials that can be used include metal materials such as aluminum, gold, platinum, and tungsten, metal oxide materials such as ruthenium oxide, and any perovskite-type conductive oxide material selected from LNF ($LaNi_{0.6}Fe_{0.4}O_3$), LSN ($LaNi_{0.6}Fe_{0.4}O_3$), LSM ($La_{1-x}Sr_xMnO_{3-\delta}$), LSC ($La_{1-x}Sr_xCoO_{3-\delta}$), LCC ($La_{1-x}Ca_xCrO_{3-\delta}$), and LSCN ($La_{0.85}Sr_{0.15}Cr_{1-x}Ni_xO_{3-\delta}$) ($0.1 \leq X \leq 0.7$).

Materials that can be used, as appropriate, for the insulating layer 100 include insulating layer materials such as alumina, magnesia, titania and mullite, dielectric materials each being a mixture of a high-dielectric constant material, such as barium titanate, with alumina or zirconia, and known ceramic materials such as partially stabilized zirconia, represented by 8YSZ $(ZrO_2)_{0.82}(Y_2O_3)_{0.08}$.

The present embodiment shows an example in which the detecting unit 13 is formed such that the cross sections of the pair of conductor layers 11 and 12 are exposed parallel to a lateral face on the tip end side of the particulate matter detection element 10 in a rectangular parallelepiped shape. However, the detecting unit 13 may be provided such that the cross sections of the pair of conductor layers 11 and 12 are exposed from a bottom surface on the tip end side of the element 10.

In FIGS. 1A to 1C, different hatchings are used to clarify that the pair of conductor layers 11 and 12 are alternately laminated and the polarities are alternated. The different hatchings are not used for discriminating the materials of the conductor layers 11 and 12.

Referring to FIG. 1C, an inner structure of the element 10 will be more specifically described.

The insulating layer 100 is formed into a flat shape by a known manufacturing method, such as doctor blading, with through holes being punched, as necessary, in predetermined positions to thereby form through hole electrodes 114 and 124.

The pair of conductor layers 11 and 12 are configured by the planar portions 110 and 120 which are provided with the end edge portions 111 and 121 using a manufacturing method described hereafter, lead portions 112 and 122 connected to the outside, terminal portions 113 and 123, and through hole electrodes 114, 124, and 125.

The through hole electrodes 114 and 124 electrically conduct the planar portions 110 and 120 having the same polarity.

The lead portions 112 and 122, the through hole electrodes 114 and 124, and the terminal portions 113 and 123 are formed by a manufacturing method, such as known thick-film printing.

A laminated structure is used for the element 10. Specifically, in the laminated structure, several conductor layers 11 and 12 are laminated on respective insulating layers 100 such that the conductor layers 11 and 12 are alternated. The present embodiment includes a lowermost insulating layer 100H which is provided with a heating element 140 that generates heat by energization and a pair of lead 141 and terminal 142 for electrically conducting the heating element 140, thereby configuring a heating unit 14.

For the heating element 140, a known heating resistor material such as tungsten, molybdenum silicide, or ruthenium oxide is used. For the lead 141 and the terminal 142, a known electrically conductive metal material such as gold, platinum, or tungsten is used. A known method, such as thick-film printing, is used for forming these components.

The element 10 is integrally formed by baking.

In forming the detecting unit 13 of the present embodiment, the element 10, after being laminated and baked, is appropriately cut such that a cross section thereof is exposed to a lateral side face thereof, followed by polishing.

Referring now to FIGS. 2A, 2B, 2C, 2D, 3A, 3B, 3C, and 3D, hereinafter are described comparative example 1, example 1, example 2, example 3, comparative example 2, example 4, example 5, and example 6 through the study of which the advantageous effects of the present disclosure have been confirmed.

A basic structure of both the comparative examples and the examples is a laminated structure similar to that of example 1 shown in FIG. 1C. In the description below, for clarity's sake, corresponding portions are represented by reference signs suffixed with z, y, x, and w for comparative examples 1, 2, 3, and 4, and suffixed with a to g for examples 2 to 8.

Figure 2A:
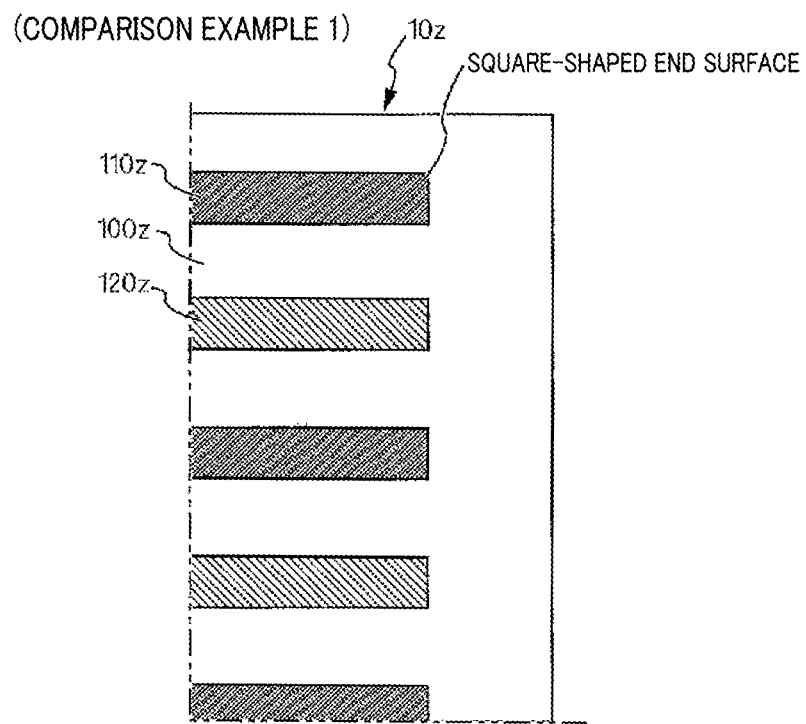
FIG. 2A is an enlarged view illustrating a major part of a conventional particulate matter detection element 10z in which an electrode layer end face is in a square shape, according to comparative example 1.

In an element 10z shown in FIG. 2A as comparative example 1, insulating layers 100z are laminated with respective conductor layers 110z and conductor layers 120z, such that the conductor layers 110z are alternated with the conductor layers 120z.

The conductor layers 110z and 120z of the comparative example 1 each have a rectangular cross section, with end faces being in a square shape and aligned.

Figure 2B:
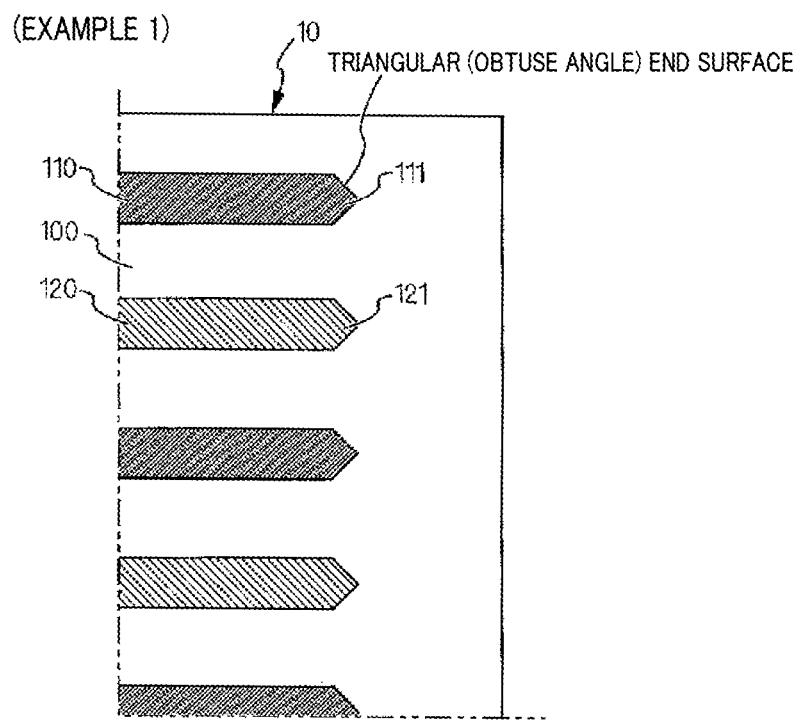
FIG. 2B is an enlarged view illustrating a major part of the particulate matter detection element 10 in which an electrode layer end face is in an obtuse-angle triangular shape, given as example 1 of the present disclosure.

In the element 10 shown in FIG. 2B as example 1, the insulating layers 100 are laminated with the respective conductor layers 110 and the conductor layers 120, such that the conductor layers 110 are alternated with the conductor layers 120.

The conductor layers 110 and 120 of example 1 have the tapered end edge portions 111 and 121, respectively, which have a triangular (obtuse angle) cross section and are aligned.

Figure 2C:
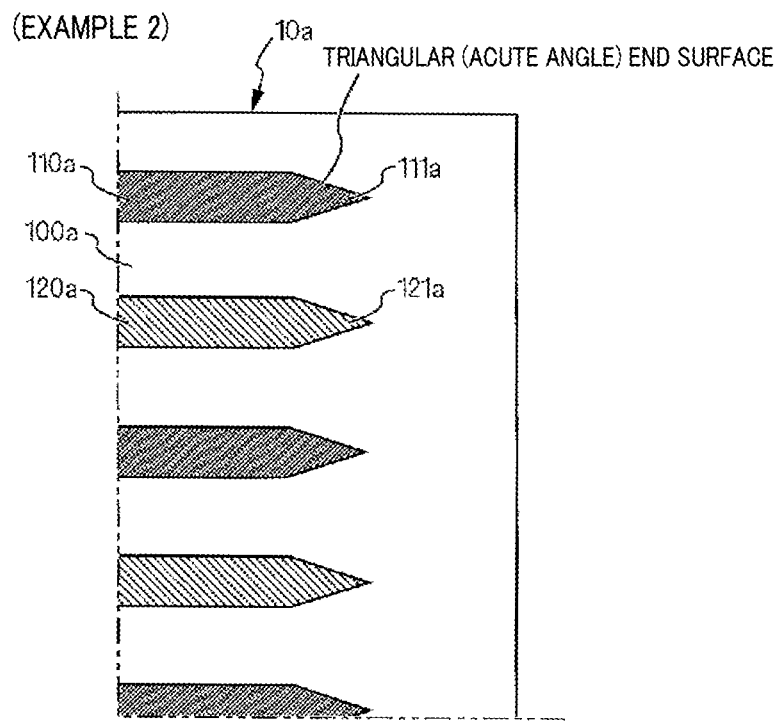
FIG. 2C is an enlarged view illustrating a major part of a particulate matter detection element 10a in which an electrode layer end face is in an acute triangular shape, according to example 2 of the present disclosure.

An element 10a shown in FIG. 2C as example 2 is different from example 1 in that end edge portions 111a and 121a have an acute triangular cross section.

Figure 2D:
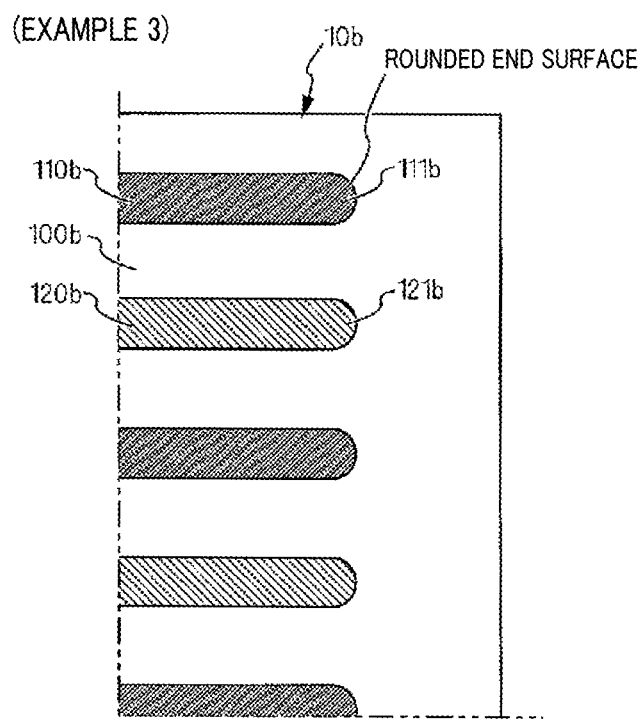
FIG. 2D is an enlarged view illustrating a major part of a particulate matter detection element 10b in which an electrode layer end face is in a circular-arc shape, according to example 3 of the present disclosure.

An element 10b shown in FIG. 2D as example 3 is different from example 1 in that end edge portions 111b and 121b are curved and have a circular-arc cross section. The element 10b is characterized in that the conductor layers each have a constant thickness, and include respective conductor layer planar portions 110b and 120b in a stripped pattern in the cross section of the element, and smoothly curved conductor layer end edge portions 111b and 121b having a circular arc cross section, provided on both sides of the respective conductor layer planar portions.

Figure 3A:
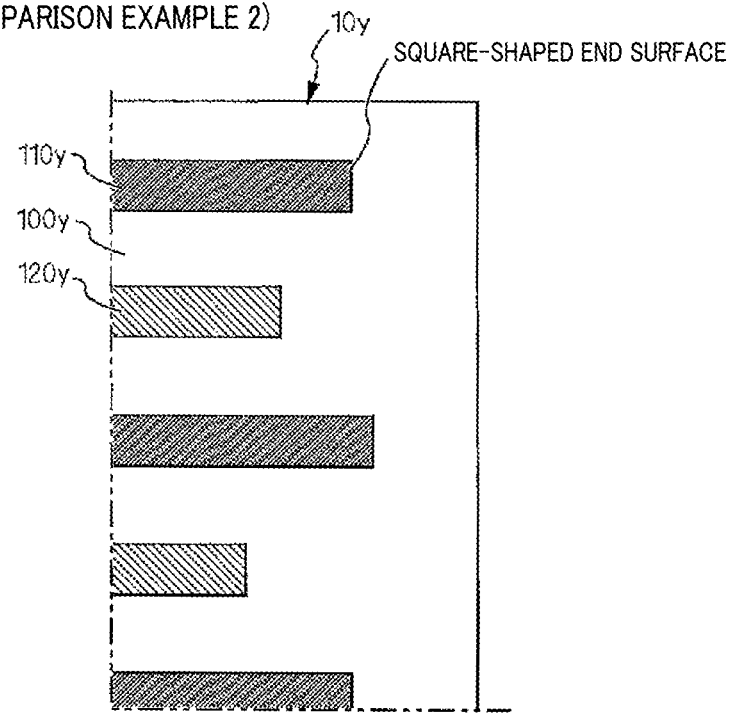
FIG. 3A is an enlarged view illustrating a major part of a conventional particulate matter detection element 10y in which an electrode layer end face is in a square shape and the end face position is not fixed, according to comparative example 2.

In an element 10y shown in FIG. 3A as comparative example 2, conductor layers 110y and 120y have square end faces similarly to comparative example 1. However, the element 10y is different from comparative example 1 in that the end faces are not aligned.

Figure 3B:
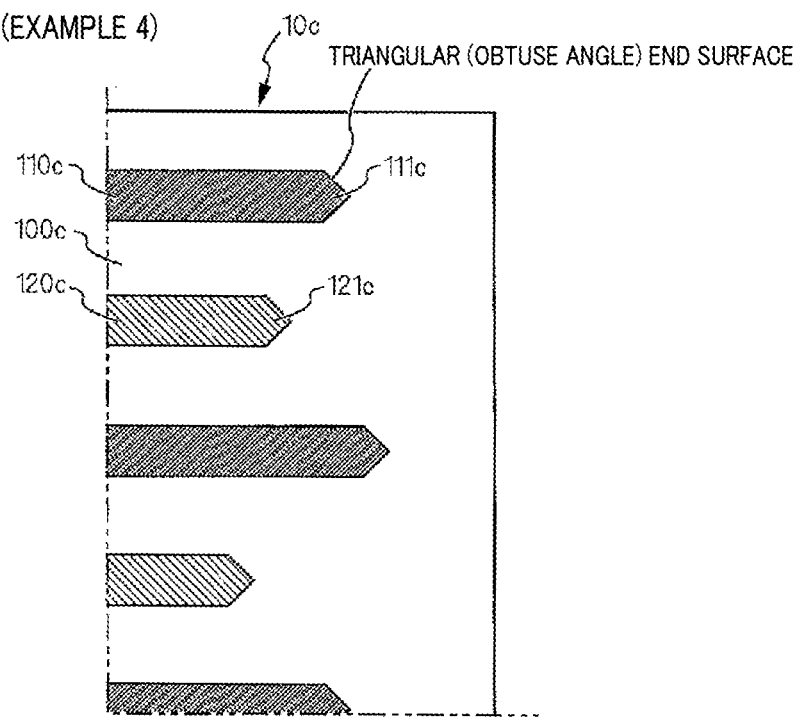
FIG. 3B is an enlarged view illustrating a major part of a particulate matter detection element 10c in which an electrode layer end face is in an obtuse triangular shape and the end face position is not fixed, according to example 4 of the present disclosure.

In an element 10c shown in FIG. 3B as example 4, conductor layers 110c and 120c are provided with tapered end edge portions 111c and 121c having a triangular (obtuse angle) cross section similarly to example 1. However, the element 10c are different from example 1 in that the end edge portions 111c and 121c are not aligned.

Figure 3C:
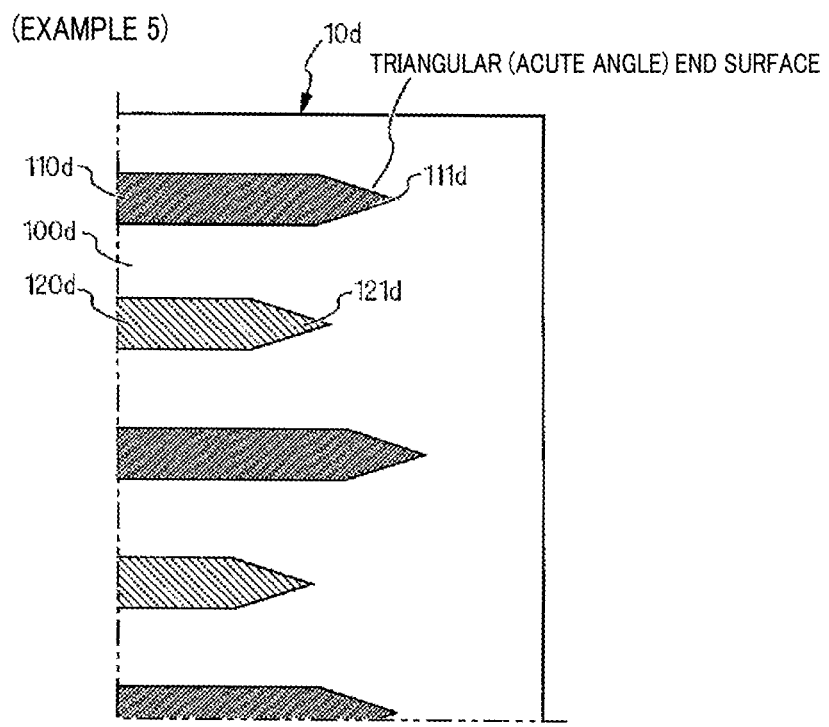
FIG. 3C is an enlarged view illustrating a major part of a particulate matter detection element 10d in which an electrode layer end face is in an acute triangular shape and the end face position is not fixed, according to example 5 of the present disclosure.

In an element 10d shown in FIG. 3C as example 5, conductor layers 110d and 120d are provided with tapered end edge portions 111d and 121d having a triangular (acute angle) cross section similarly to in example 2. However, the element 10d is different from example 2 in that the end edge portions 111d and 121d are not aligned.

Figure 3D:
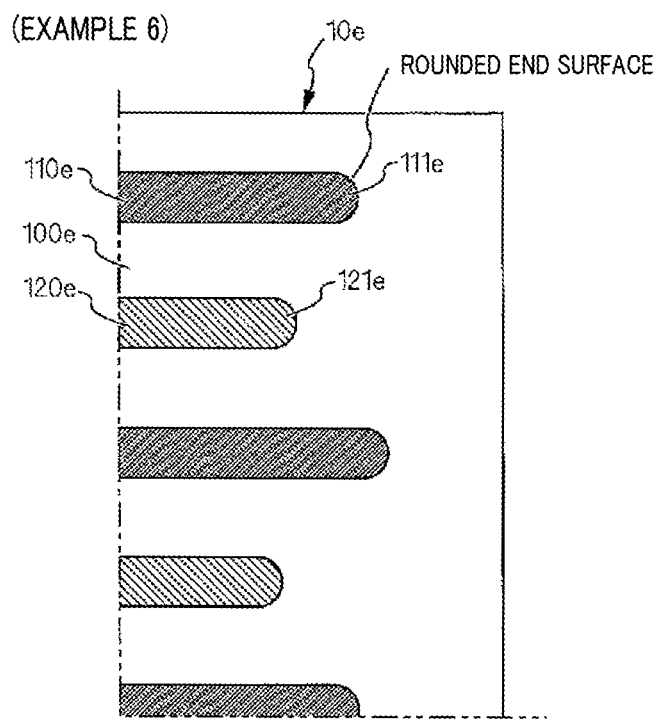
FIG. 3D is an enlarged view illustrating a major part of a particulate matter detection element 10e in which an electrode layer end face is in a circular-arc shape and the end face position is not fixed, according to example 6 of the present disclosure.

In an element 10e shown in FIG. 3D as example 6, curved end edge portions 111e and 121e have a circular-arc cross section similarly to example 3. However, the element 10e is different from example 3 in that the end edge portions 111e and 121e are not aligned.

Referring to FIGS. 4A, 4B, 4C, 4D, 5A, 5B, 5C, and 5D, hereinafter are described differences between comparative example 1, examples 1 to 3, comparative example 2 and examples 4 to 6 on the basis of simulation results, for electric field distribution generated on a detecting unit plane when a given voltage is applied across each pair of conductor layers.

Figure 4A:
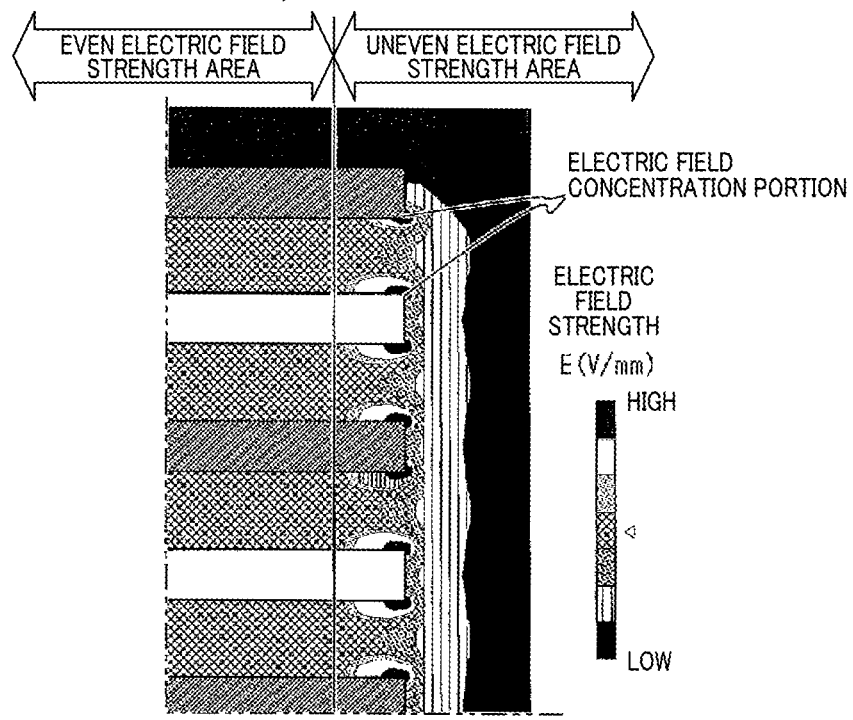
FIG. 4A is a schematic diagram illustrating electric field intensity distribution on a detecting unit plane, according to comparative example 1.

As shown in FIG. 4A, in comparative example 1, it has been found that strong electric field concentration occurs at corners of the conductor layers 11z and 12z, and the electric field intensity is relatively low in the area between a pair of planar portions 110z and 120z in which the electric field intensity is uniform.

Figure 4B:
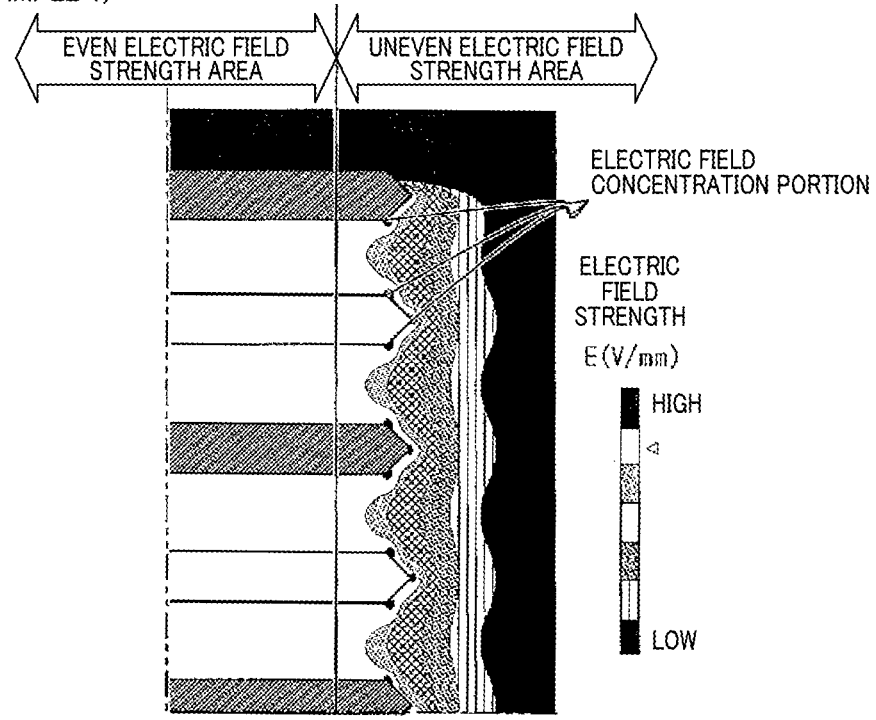
FIG. 4B is a schematic diagram illustrating electric field intensity distribution on a detecting unit plane, according to example 1.

As shown in FIG. 4B, in example 1, it has been found that the electric field concentration is dispersed into three areas in each of the end edge portions 111 and 121, the ratio of electric field concentration becomes relatively low, and accordingly, the electric field strength in the area between the planar portions 110 and 120 in which the electric field intensity is uniform becomes relatively high.

Figure 4C:
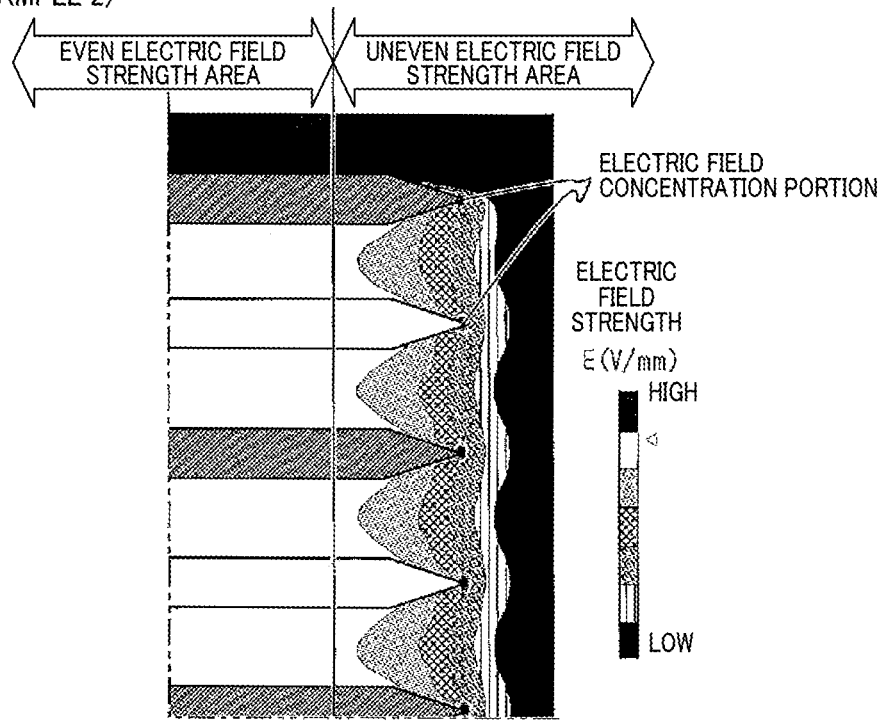
FIG. 4C is a schematic diagram illustrating electric field intensity distribution on a detecting unit plane, according to example 2.

As shown in FIG. 4C, in example 2, it has been found that the electric field concentration is further reduced, and accordingly, the electric field strength in the area between the planar portions 110a and 120a in which the electric field intensity is uniform is maximized.

Figure 4D:
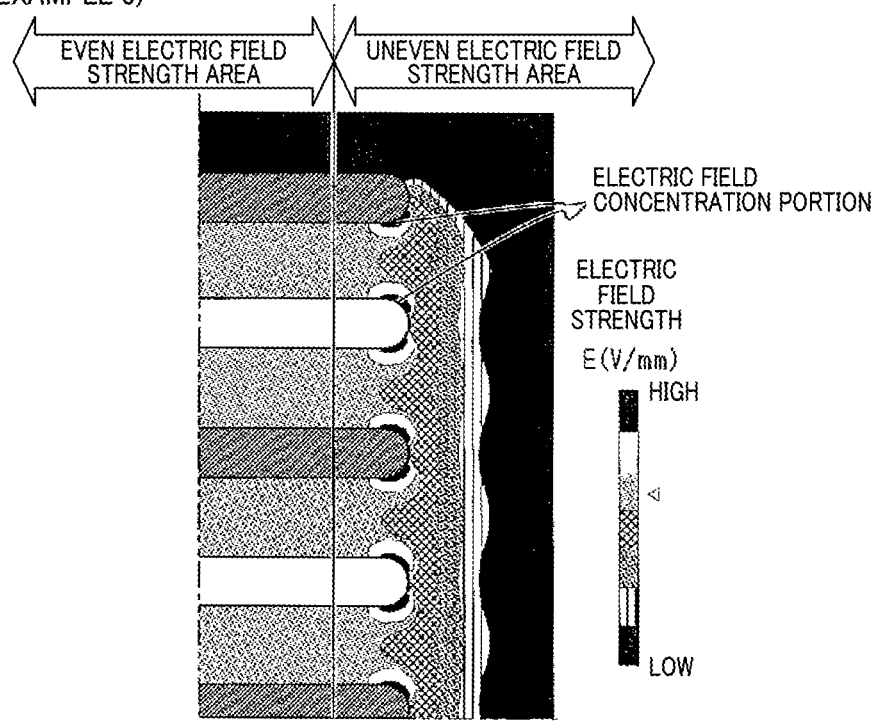
FIG. 4D is a schematic diagram illustrating electric field intensity distribution on a detecting unit plane, according to example 3.

As shown in FIG. 4D, in example 3 as well, it has been found that electric field concentration is reduced, and the electric field strength in the area between the planar portions 110b and 120b in which the electric field intensity is uniform becomes relatively high.

Figure 5A:
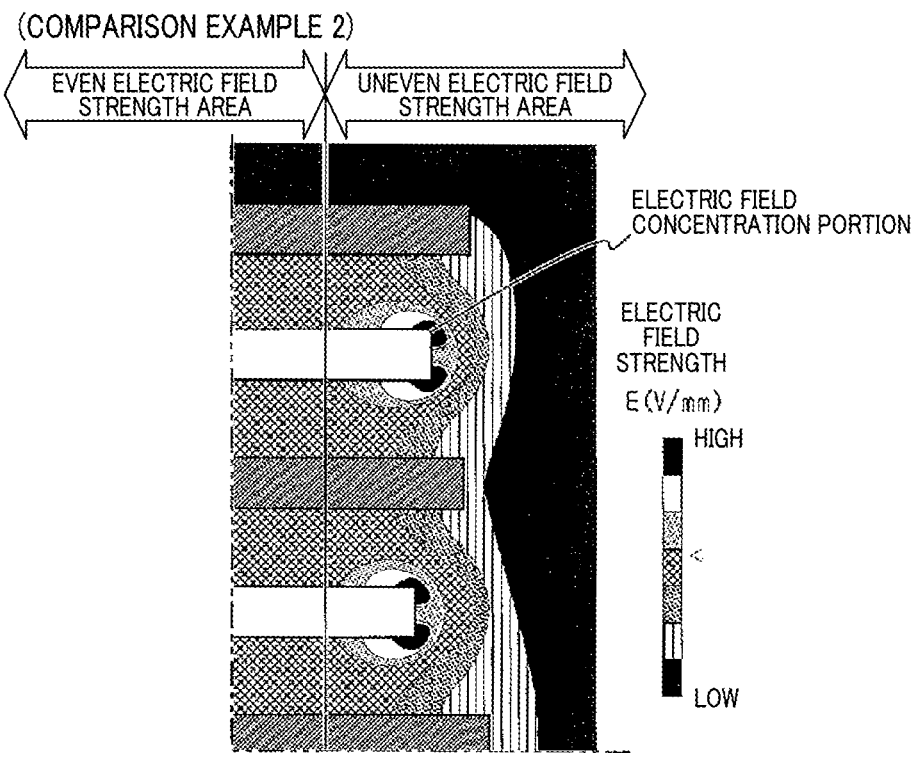
FIG. 5A is a schematic diagram illustrating electric field intensity distribution on a detecting unit plane, according to comparative example 2.
Figure 5B:
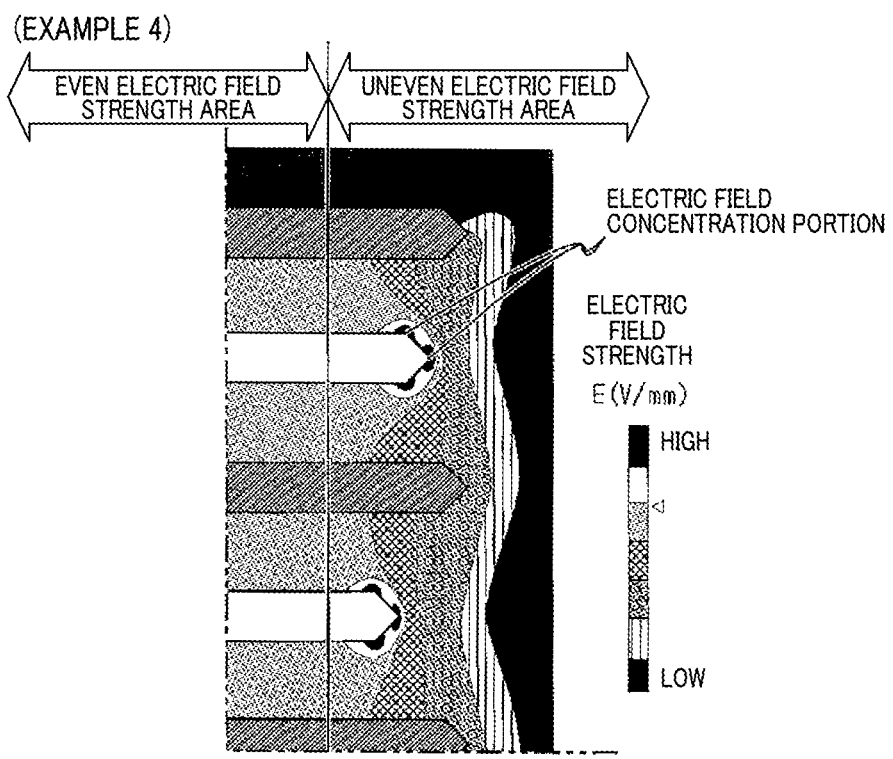
FIG. 5B is a schematic diagram illustrating electric field intensity distribution on a detecting unit plane, according to example 4.

In the case where the end faces are not aligned, as shown in FIG. 5A, in comparative example 2, it has been found that the electric field concentration is more reduced than in comparative example 1, and the electric field intensity in the area between the planar portions 110y and 120y in which the electric field intensity is uniform becomes relatively higher than in comparative example 1.

On the other hand, in examples 4 and 5, it has been found that more electric field concentration is caused than in examples 1 and 2, and the electric field intensity in the areas between the planar portions 110c and 110d, and between 120c and 120d in which the electric field intensity is uniform becomes relatively lower than in examples 1 and 2.

However, in example 6, it has been found that the electric field concentration is more reduced than in example 3, and the electric field intensity in the area between the planar portions 110e and 120e in which the electric field intensity is uniform becomes relatively higher than in example 3.

Figure 6:
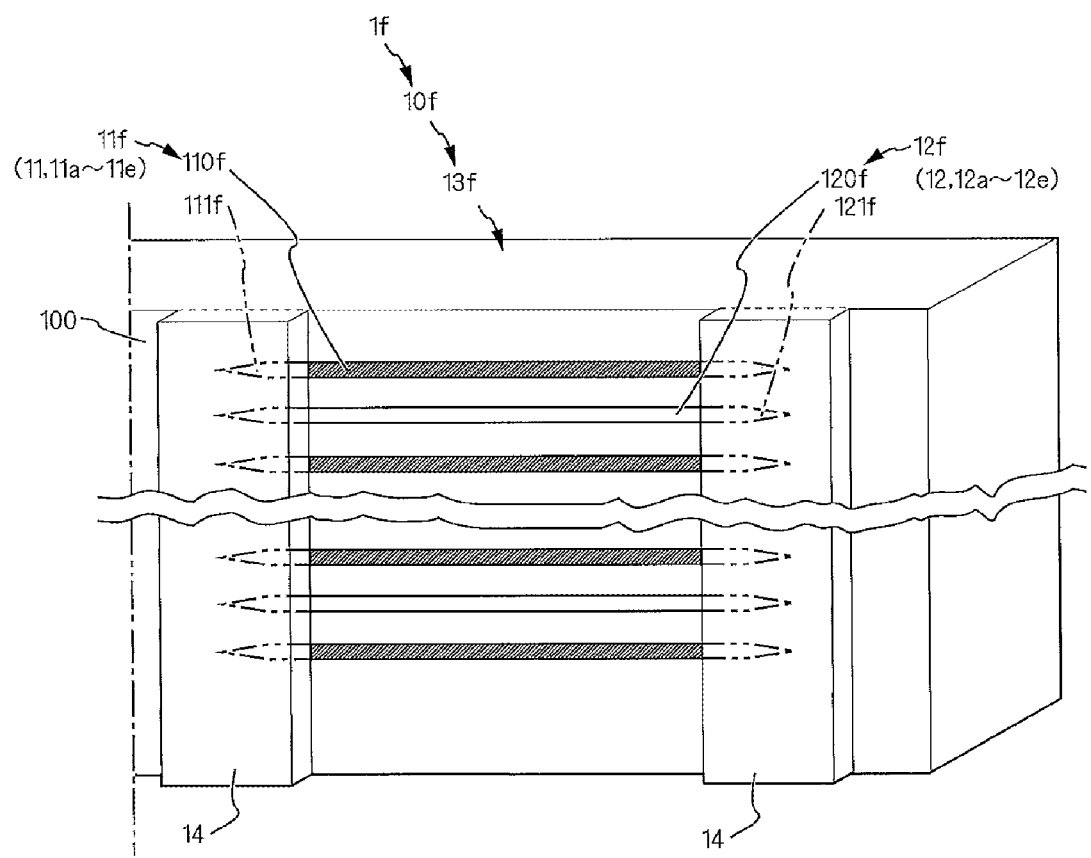
FIG. 6 is an enlarged schematic perspective view illustrating a detecting unit 13f, according to example 7.

Referring to FIG. 6, an element 10f of example 7 of the present disclosure will be described.

In the present example, a shielding layer 14 is provided to the detecting unit 13f to cover all the end edge portions 111f and 121f and part of the planar portions 110f and 120f, that is to say, to cover the areas where the electric field intensity is non-uniform. The shielding layer 14 is made of a known insulating material, such as glass or alumina, or the same material as the insulating layer 100.

The configuration provided with the shielding layer 14 can also be used in any of the foregoing examples 1 to 6.

Figure 7A:
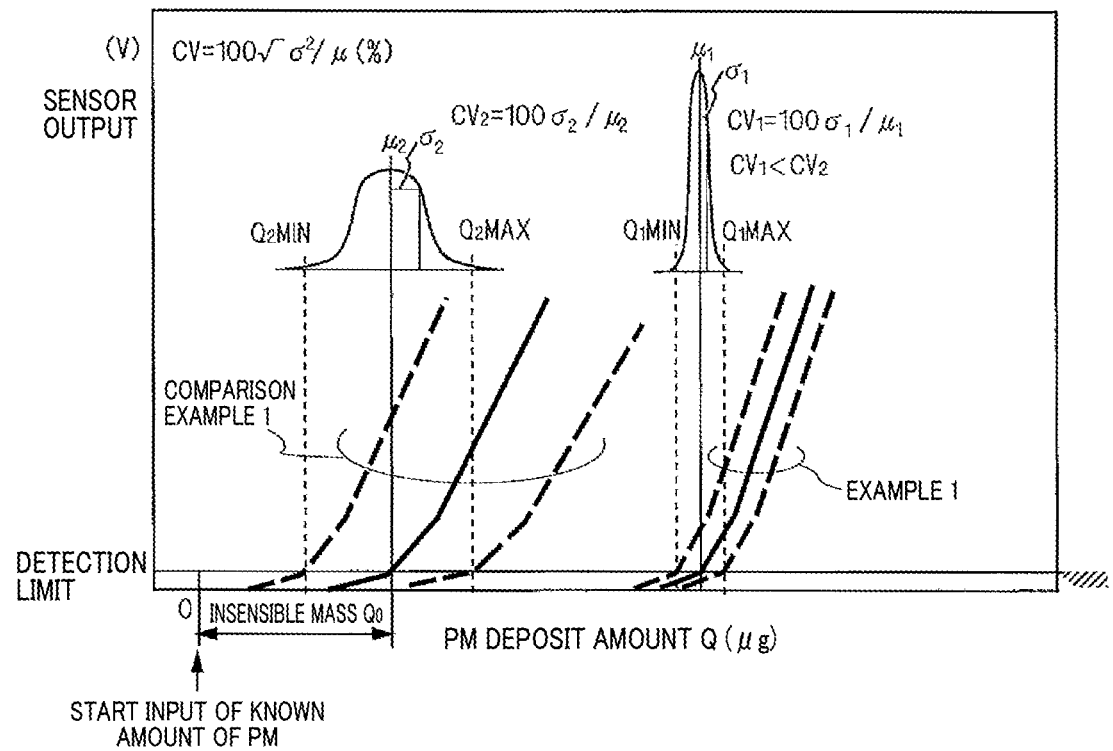
FIG. 7A is a characteristics diagram illustrating variation in sensor output, according to comparative example 1 and example 1.
Figure 7B:
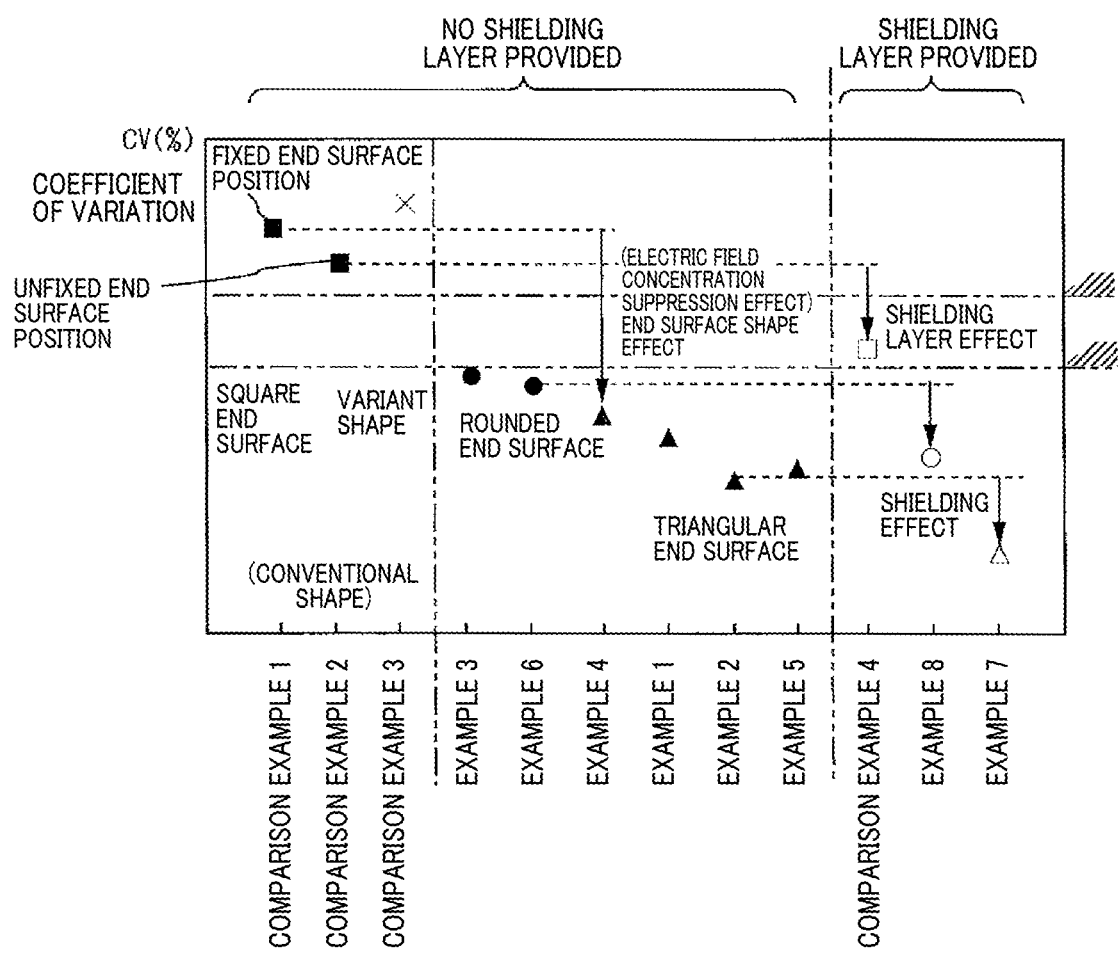
FIG. 7B is a characteristics diagram illustrating effects of reducing variation of insensible mass, according to several comparative examples and the present disclosure.

Referring now to FIGS. 7A and 7B, the results of the tests conducted to confirm the advantageous effects of the present disclosure will be described. Let us assume the case where the detecting unit 13 of the element 10 is located in a flow path of a gas to be measured and exposed to a gas, with a predetermined voltage being applied to the detecting unit 13 from the power supply 2, and with a known amount of particulate matter being permitted to flow. In this case, there is an insensible mass $Q_0$ (dead period) for which the particulate matter cannot be detected until a fixed amount or more of the particulate matter is deposited in the detecting unit 13.

In addition to comparative examples 1 and 2, and examples 1 to 7, the following examples and comparative examples were also prepared. For each of the examples and comparative examples, several samples were prepared and a given amount of particulate matter was inputted to the samples to measure the insensible mass $Q_0$. The examples and comparative examples additionally prepared were: comparative example 3 obtained by forming conductor layers similar to those of comparative example 1 without forming intermediate layers; comparative example 4 obtained by providing the shielding layer 14 mentioned above to comparative example 2; and example 8 obtained by providing a shielding layer to example 6.

As shown in FIG. 7A, in comparative example 1, it has been found that an average value $\rho_2$ of the insensible masses $Q_0$ is small and the particulate matter is detectable at an early stage, but a variation $\sigma_2$ between the samples is great.

On the other hand, in example 1, it has been found that the average value $\mu_1$ of the insensible masses $Q_0$ is greater than that of the insensible masses in comparative example 1, but the variation $\delta_1$ between the samples is much smaller.

The reason for this is estimated to be that, in comparative example 1, a high concentration of the electric field occurs at the corners of the end faces of the conductor layers 11z and 12z, the particulate matter is attracted to the electric charge collected on the surfaces at the corners and locally deposited, and the local deposition forms a conduction path at an early stage.

However, the electric field concentration at the corners greatly varies between the samples and is considered unstable.

Therefore, the samples have been evaluated using a variation coefficient. Specifically, each sample is evaluated by calculating a variation coefficient CV $(100\sqrt{\sigma^2}/\mu)$ (%). The evaluation results are shown in FIG. 7B.

As can be seen, the variation in comparative example 2 is smaller than in comparative example 1 but, in all examples 1 to 7, the variation coefficient can be made smaller than in comparative examples 1 to 4. Thus, it will be understood that the present disclosure has an effect of improving reliability as a sensor.

It is considered that concentration of the electric field and local deposition of particulate matter in the end portions of the conductor layers 11 and 12 are reduced by providing the end edge portions 111, 121, 111a, 121a, 111b, 121b, 111c, 121c, 111d, 121d, 111e, and 121e having a triangular or circular-arc cross section to both end faces of the respective conductor layers 11 and 12.

In the end edge portions 111a and 121a having an acute triangular cross section, there is a large distance between the apexes at which electric field concentration tends to occur. This is considered to be the reason why a long time is taken for forming the conduction path between the pair of end edge portions 111a and 121a.

The following description sets forth methods of manufacturing the particulate matter detection elements 10z, 10y, 10, and 10a provided as the foregoing comparative examples 1 and 2, and examples 1 and 2. In the following description, FIGS. 8A, 8B, 8C and 8D are referred to.

Comparative example 1 shows a basic method of manufacturing the particulate matter detection element 10z in which a cross section of the alternate lamination of the conductor layers 11z and 12z and the insulating layers 100z is used as the detecting unit 13z.

An insulating material, such as alumina, is mixed with a known binder, plasticizer, dispersant, solvent, and the like, and stirred to form a slurry. The slurry is formed into a sheet shape by a known manufacturing method, such as doctor blading, thereby obtaining an insulating sheet 100zGS.

In a punching step P0z, not shown, the insulating sheet 100zGS is punched using a die or the like to form in advance, as required, an alignment guide for printing, through holes for embedding through hole electrodes 114z and 124z that connect conductor layers of the same polarity, and the like, and the insulating sheet 100zGS is punched out into a predetermined outer shape.

In a printing step P1z, a conductor paste is injected from a thick-film printing screen in which a predetermined conductor pattern is formed to transfer conductor layer printed films 11zPRT and 12zPRT to the insulating layer sheets 100zGS.

At this time, as shown being enlarged in the circle, due to the effects of the rheological characteristics and surface tension of the paste, the film thickness near the center is reduced and the film thickness near the outer periphery is increased, although very slightly.

In comparative example 1, intermediate layer 101z is formed by thick-film printing, using a paste containing the same materials as the insulating material for forming the insulating layer 100z, so as to cover portions except for the conductor layers. The intermediate layer 101z has the same thickness as that of the conductor layer printed films 11zPRT and 12zPRT.

In the subsequent laminating and pressure-bonding step P2z, the insulating layer sheets 100zGS are laminated such that the polarities of the conductor layer printed films 11zPRT and 12zPRT are alternated, followed by pressure-bonding using a die or the like.

In a baking step P3z, a laminated structure obtained in this way is integrated by simultaneously baking the conductor layers 11z and 12z and the insulating layers 100z.

Subsequently, the integrated object is cut and polished, for example, to expose cross sections of the conductor layers 11z and 12z forming the detecting unit 13, thereby completing the element 10z.

In comparative example 1, due to the provision of the intermediate layer 101z, the conductor layer printed films 11zPRT and 12zPRT and the conductor layer sheet 110z are hardly deformed during lamination and pressure bonding, and the mechanical strength of the element 10z is good. The conductor layers 11z and 12z retain the stripped-pattern cross section.

However, it has been found that, when a voltage is applied across the conductor layers, concentration of the electric field at the corners is great, and as described above, variation in insensible mass is great.

The element 10y shown as comparative example 2 is based on a manufacturing method similar to that of comparative example 1. In the laminating and pressure-bonding step, the conductor layers 11y and 12y are laminated with the end faces thereof being misaligned as designed.

Referring to FIG. 8B, an outline of a manufacturing process for the element 10x as comparative example 3 and problems of comparative example 3 will be described.

In comparative example 3, as shown in a printing step P1x, only the conductor layers 110x and 120x are printed on an insulating layer sheet 100xGS that has been punched out into a predetermined shape. Thus, without providing an intermediate layer, the manufacturing process proceeds to a laminating and pressure-bonding step P2x.

Conductor layer printed films 11xPRT and 12xPRT are harder than the insulating layer sheets 100xGS. Therefore, in the laminating and pressure-bonding step P2x, the insulating layer sheets 100xGS are elastically deformed when they are laminated and pressure-bonded. Resultantly, the insulating layer sheets 100xGS are adhered to each other, embedding the conductor layer printed films 11xPRT and 12xPRT therebetween.

At this time, as shown being enlarged in the circle of FIG. 8B illustrating the laminating and pressure-bonding step P2x, gaps each having a triangular cross section are formed on both sides of the conductor layer printed films 11xPRT and 12xPRT.

Through the subsequent baking step P3x, the laminated body is sintered and the gaps are reduced as a result of the surface areas of the gaps being reduced. However, the gaps are not completely eliminated and some remains as voids. Thus, there is a concern that the gaps can trigger delamination.

Further, the end faces of the conductor layers 11x and 12x after baking become polygonal or irregularly shaped. Thus, similarly to comparative example 2, concentration of the electric field at the corners is easily caused.

Referring to FIG. 8C, an outline of a manufacturing process of example 1 of the present disclosure will be described.

According to the present embodiment, a process similar to that of comparative example 1, i.e., a punching step P0, is performed to punch an alignment guide and through holes, as required, in an insulating layer sheet 100GS and to punch the insulating layer sheet 100GS into a predetermined outer shape. In the punching step P0, simultaneously with punching the insulating layer sheet 100GS, a recessed sheet 100PCD is formed. The recessed sheet 100PCD is provided with a recess 101 at the position corresponding to the position where the conductor layer 110 or 120 is formed by printing. The recess 101 is in conformity with the predetermined shape of the conductor layer end edge portion 111 or 121.

Specifically, the punching die is provided with a protrusion for forming the recess 101, and the surface of the insulating layer sheet 100GS is pressed against the die.

Thus, a tapered surface that is sloped at a desired angle can be formed in the portion in which the conductor layer end edge portion 111 or 121 is formed.

As a result, if normal thick-film printing is performed in a printing step P1, the conductor layer end edge portion 111 or 121 side to be in contact with the insulating layer sheet 100GS is sloped conforming to the shape of the recess 101.

Further, since the recess 101 is also formed on the underside of the recessed sheet 100PCD, when the recessed sheets are laminated in the laminating and pressure-bonding step P1, adhesion is improved between the conductor layer printed films 110 and 120, forming no voids, unlike in comparative example 2.

Furthermore, if an intermediate layer as used in comparative example 1 is not provided, the insulating layer sheets 100GS can be easily adhered to each other.

As a result, when the conductor layers 11 and 12 and the insulating layers 100 are integrated in a baking step P3, the element 10 hardly causing delamination can be formed.

In addition, since the conductor layer end edge portions 111 and 121 can be formed into a tapered shape having a triangular cross section, the element 10 that can reduce concentration of the electric field can be easily realized.

Referring to FIG. 8D, an outline of a manufacturing process of example 2 of the present disclosure will be described.

A conductor printing step P1a according to the present embodiment is different from the foregoing embodiments in that partially changed opening-ratio printing screens PPM and PPMA are used when the conductor layers 11 and 12 are printed on the insulating layer sheet 100(GS). In the partially changed opening-ratio printing screens PPM and PPMA, a mesh opening ratio is partially changed such that the film thickness resulting from the printing is reduced at predetermined positions.

Figure 9A:
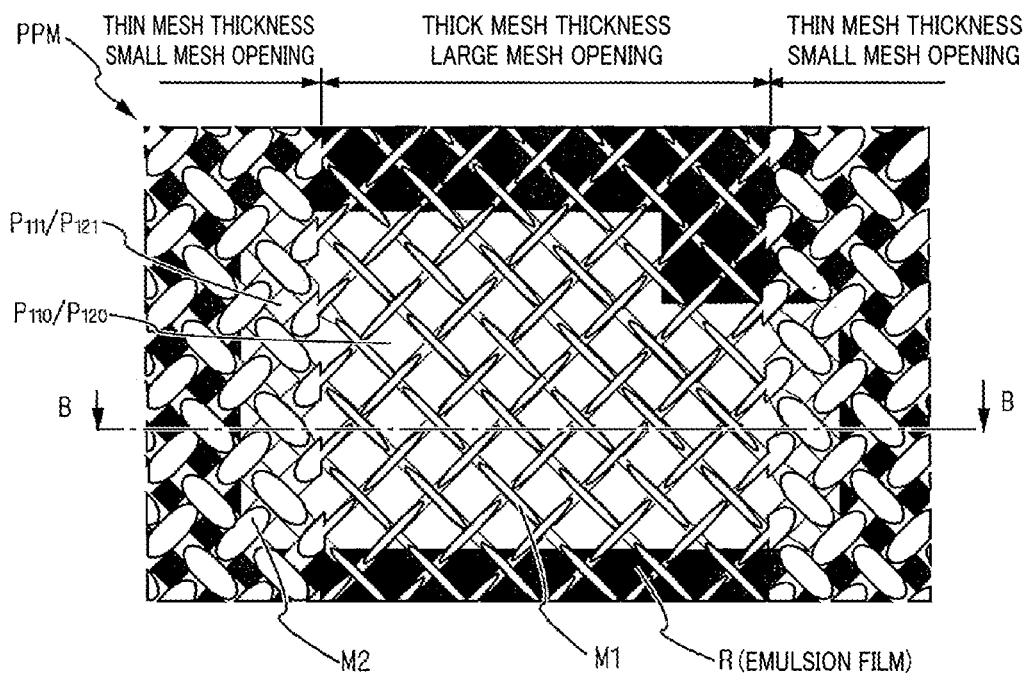
FIG. 9A is a schematic plan view illustrating a thick-film printing screen used in manufacturing the particulate matter detection element of the present disclosure.
Figure 9B:
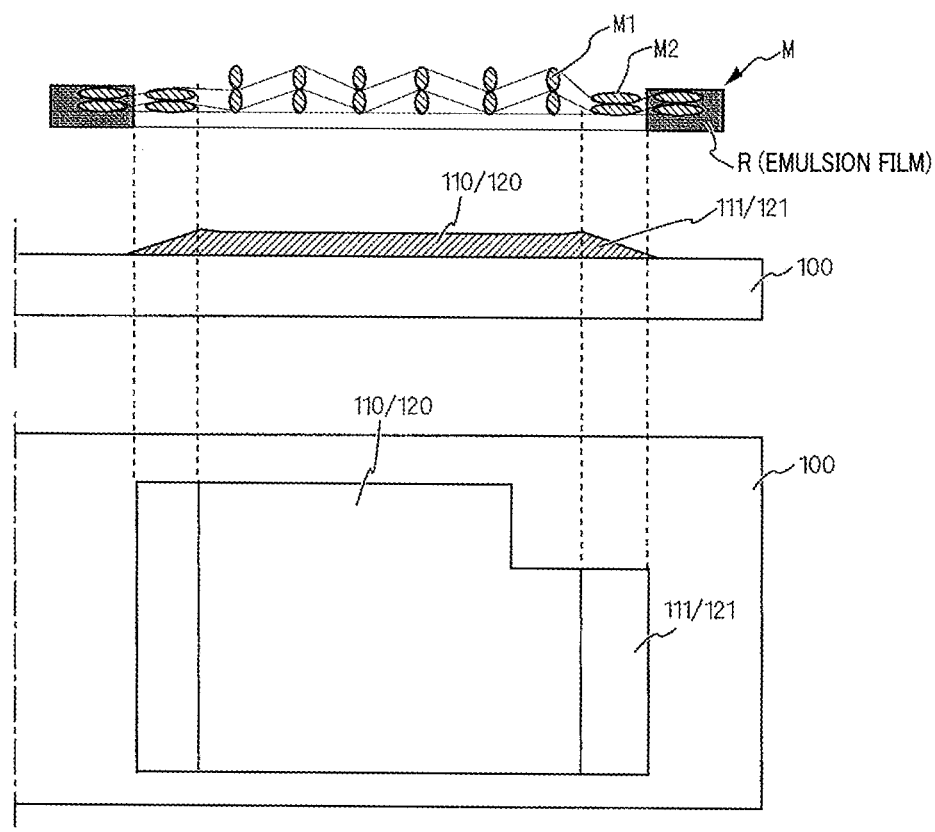
FIG. 9B is a set of diagrams including a cross-sectional view taken along the line B-B of FIG. 9A, and cross-sectional and plan views illustrating an insulating layer with a conductor layer being formed corresponding to the B-B cross-sectional view.
Figure 10:
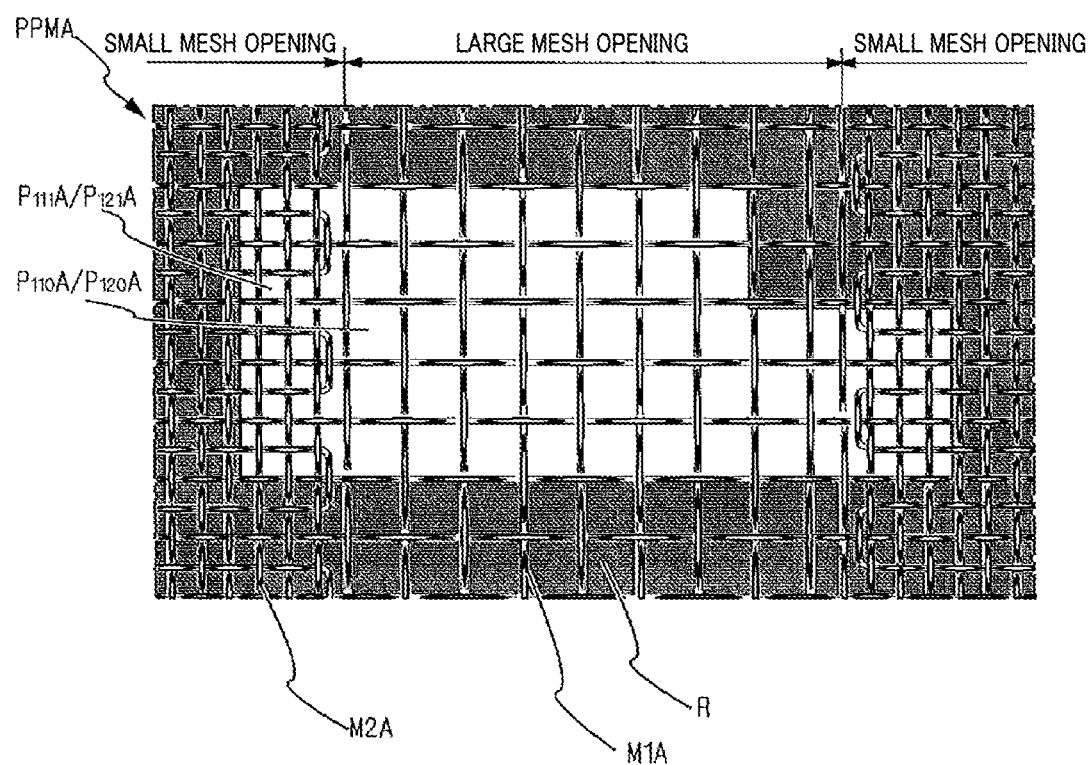
FIG. 10 is a plan view illustrating a modification of the thick-film printing screen used in the present disclosure.

Referring to FIGS. 9A, 9B, and 10, the partially changed opening-ratio printing screens PPM and PPMA will be described. According to the present embodiment, the partially changed opening-ratio printing screen PPM used can reduce the amount of conductor paste injected from the portions where the opening ratio is designed to be low. Thus, the thickness of the conductor layer formed can be reduced, enabling formation of the conductor layer end edge portions 111a and 121a tapered outward with acutely-angled sloped surfaces and having a triangular cross section.

As described above, the conductor layers 11a and 12a having the conductor layer end edge portions 111a and 121a with a triangular cross section are formed in the insulating layer sheets 100GS. Further the insulating layer sheets 100GS are laminated and pressure-bonded using a die or the like. Thus, the insulating layers 100GS are brought into intimate contact with each other, embedding the conductor layers 11a and 12a therebetween.

At this time, since the conductor layer end edge portions 111a and 121a are tapered and has a triangular shape, gaps as in comparative example 2 are not formed.

Further, the laminated structure prepared in this way is baked in a baking step P3a. Thus, the element 10a reducing concentration of the electric field near the conductor end faces can be quite easily formed.

Referring to FIGS. 9A and 9B, hereinafter are described characteristics of a partially reduced opening-ratio screen M used in manufacturing the particulate matter detection element 10 of the present disclosure, and the shape of the conductor layers 11 and 12 formed by using the screen M.

It should be noted that the drawings to be referred to show only a pattern for forming the conductor layer planar portion 110 and the conductor layer end edge portion 111 in one of the pair of conductor layers 11 and 12. The pattern for forming the conductor layer planar portion 120 and the conductor layer end edge portion 121 of the other conductor layer corresponds to a left-and-right reverse of the pattern of the firstly mentioned conductor layer. Therefore, the following description is provided omitting the secondly mentioned conductor layer and using a combined reference sign 110/120 for the common configuration.

The partially reduced opening-ratio screen M used in the present embodiment is obtained by partially rolling and smoothing a thick-film printing screen generally used in thick-film printing and by reducing a mesh thickness and mesh opening ratio.

A resist film R is formed into a predetermined printed pattern by coating an emulsion onto a printing screen, followed by exposure with a pattern conforming to the configuration of the conductor layer planar portions 110 and 120, and further followed by curing.

As shown in FIGS. 9A and 9B, in a mask M2, portions where the conductor layer end edge portions 111 and 121 are printed have a large thickness in the cross-sectional direction and a large line width in the planar direction. Therefore, the opening ratio of the portions where the conductor layer end edge portions 111 and 121 are printed, that is, opening ratios $P_{111}$ and $P_{121}$ for forming the end edge portions are lower than the opening ratio of a mask M1 used for portions where the conductor layer planar portions 110 and 120 are formed, that is, opening efficiency $P_{110}$ and $P_{120}$ of forming a planar portion.

Therefore, as shown in FIG. 9B, when the conductor layer planar portions 110 and 120 are printed, the amount of paste injected from the mask M2 is reduced, and the thickness of the conductor layer end edge portions 111 and 121 becomes smaller than the thickness of the conductor layer planar portions 110 and 120.

Referring to FIG. 10A, a modification MA of the partially reduced opening-ratio screen will be described.

The foregoing embodiment has shown, as an example, the partially reduced opening-ratio screen M in which part of the thick-film printing screen is pressed to reduce the opening ratio. However, as shown in FIG. 10, in a partially reduced opening-ratio screen MA, an opening ratio $P_{111}A/P_{121}A$ for forming an end edge portion can be design to be lower than an opening ratio $P_{110}A/P_{120}A$ for forming a planar portion, by increasing a weave density of lateral and vertical threads of a mask M2A for printing the conductor layer end edge portions 111 and 121, compared to a mask M1A for printing the conductor layer planar portions 110 and 120.

In the partially reduced opening-ratio screen MA of the present embodiment, the resist R is formed into a predetermined conductor pattern on a screen mesh whose opening ratio is partially adjusted in advance.

Thus, when the conductor layers 11 and 12 are printed, the amount of conductor paste injected from the mask M2A is reduced in the conductor layer end edge portions 111 and 121, thereby forming the conductor layer end edge portions 111 and 121 with a thickness smaller than the conductor layer planar portions 110 and 120. Further, by gradually increasing the weave density outward, the conductor layer end edge portions 111 and 121 can be gradually thinned outward, thereby forming the tapered end edge portions with a triangular cross section.

The foregoing embodiments have shown methods by which the conductor layer end edge portions 111 and 121 can be formed into a desired shape in the punching step P0 and in the printing step P1. These methods may be combined.

In the laminating and pressure-bonding step, the conductor layers 11 and 12 have been laminated and pressure-bonded after being dried, as an example. However, the conductor layers 11 and 12 may be laminated and pressure-bonded in an undried state.

In particular, when the recess 10 is provided in the insulating layer sheet 100(GS) in the punching step P0, and when the conductor layers 11 and 12 are laminated and pressure-bonded in an undried state, the conductor layers 11 and 12 are deformed in a fluid manner conforming to the shape of the recess 10. Therefore, the conductor layer end edge portions 111 and 121 can be formed into a desired shape.

The foregoing embodiments have shown the methods in which the intermediate layer 101 made of an insulating material as in comparative example 1 is not used in the laminating and pressure-bonding process P3. However, when the conductor layer end edge portions 111 and 121 is formed into a tapered shape with a triangular cross section or a gently curved shape with a circular-arc cross section in advance, the intermediate layer 101 may be printed using a paste made of an insulating material, in the printing step.

Use of the intermediate layer 101 can mitigate the shear stress applied to the insulating layer sheet 100 during lamination and pressure-bonding, or can improve mechanical strength of the element 10, or can minimize formation of cracks in the baking step.

In addition to the improvement in detection accuracy, an effect of improving durability of the element 10 can be expected.

REFERENCE SIGNS LIST 1 particulate matter detection sensor
10 particulate matter detection element
100 insulating layer
11, 12 conductor layer
110, 120 conductor layer planar portion
111, 121 conductor layer end edge portion
13 detecting unit
14 shielding layer
2 power supply unit
3 measuring unit
P0 punching step
P1 conductor layer printing step
P2 laminating and pressure-bonding step
P3 baking step
$P_{111}$, $P_{111}A$, $P_{121}$, $P_{121}A$ opening ratio for forming an end edge portion
$P_{110}$, $P_{110}A$, $P_{120}$, $P_{120}A$ opening ratio for forming a planar portion
M, MA partially reduced opening-ratio screen

The invention claimed is:

1. A particulate matter detection element for measuring electrical characteristics changing with an amount of deposited particulate matter, and for detecting particulate matter in a gas to be measured, the electrical characteristics being measured by a measuring unit electrically connected to the particulate matter detection element, the particulate matter detection element comprising:
   flat-shaped conductor layers;
   flat-shaped insulating layers;
   a laminated structure in which the conductor layers and the insulating layers are alternately laminated in a thickness direction thereof, the laminate structure being formed over the entire part of the particulate matter detection element in a longitudinal direction thereof; and
   a detecting unit formed of a cross section of the laminated structure, including the conductor layers having different polarities to form a pair of electrodes, particulate matter being deposited on the detecting unit, and electrical characteristics between pair of electrodes changing depending on an amount of the particular matter deposited on the detecting unit, wherein
   the conductor layers each have a constant thickness, and include conductor layer planar portions having a stripped-pattern cross section, and tapered conductor layer end edge portions each having a triangular cross section, provided on both sides of the respective conductor layer planar portions.

2. The particulate matter detection element according to claim 1, further comprising a shielding layer made of an insulating material and covering all the conductor layer end edge portions and part of the conductor layer planar portions.

3. The particulate matter detection element according to claim 2, wherein the shielding layer extends in a thickness direction of the conductor layers to cover all the conductor layer end edge portions and part of the conductor layer planar portions.

4. The particulate matter detection element according to claim 1, wherein
   the conduction layers having the same polarity are electrically connected by a through hole electrode to allow electrical connection to the measuring unit.

5. The particulate matter detection element according to claim 1, wherein
   the conduction layers having the same polarity are electrically connected at a side surface connection portion provided at a side surface of the particulate matter detection element to allow electrical connection to the measuring unit.

6. A particulate matter detection element for measuring electrical characteristics changing with an amount of deposited particulate matter, and for detecting particulate matter in a gas to be measured, the particulate matter detection element comprises:
flat-shaped conductor layers;
flat-shaped insulating layers;
a laminated structure in which the conductor layers and the insulating layers are alternately laminated; and
a detecting unit having the conductor layers of different polarities as a pair of detection electrodes on a cross section of the laminated structure, and deposited with particulate matter, wherein
the conductor layers each have a constant thickness, and include conductor layer planar portions having a stripped-pattern cross section, and gently curved conductor layer end edge portions each having a circular-arc cross section, provided on both sides of the respective conductor layer planar portions.

7. A particulate matter detection sensor that detects particulate matter present in a gas to be measured, comprising:
a particulate matter detection element for measuring electrical characteristics changing with an amount of deposited particulate matter, and for detecting the particulate matter, the detection element including: flat-shaped conductor layers; flat-shaped insulating layers; a laminated structure in which the conductor layers and the insulating layers are alternately laminated; and a detecting unit having the conductor layers of different polarities as a pair of detection electrodes on a cross section of the laminated structure, and deposited with particulate matter, wherein
the conductor layers each have a constant thickness, and include conductor layer planar portions having a stripped-pattern cross section, and tapered conductor layer end edge portions each having a triangular cross section, provided on both sides of the respective conductor layer planar portions;
a power supply that applies a voltage across the pair of detection electrodes; and
a measuring unit that allows an electric field to act on particulate matter present in the gas to be measured for collection to the detecting unit, the electric field being generated by applying a voltage across the detection electrodes by the power supply, and measures electrical characteristics between the pair of detection electrodes, the electrical characteristics changing with deposition of particulate matter on the detecting unit.

* * * * *